US010548921B2

(12) United States Patent
Leen et al.

(10) Patent No.: US 10,548,921 B2
(45) Date of Patent: Feb. 4, 2020

(54) REVERSING THE EFFECTS OF THE TUMOR MICROENVIRONMENT USING CHIMERIC CYTOKINE RECEPTORS

(75) Inventors: Ann Marie Leen, Bellaire, TX (US); Juan F. Vera, Bellaire, TX (US)

(73) Assignee: BAYLOR COLLEGE OF MEDICINE, Houston, TX (US)

( * ) Notice: Subject to any disclaimer, the term of this patent is extended or adjusted under 35 U.S.C. 154(b) by 0 days.

(21) Appl. No.: 14/110,582

(22) PCT Filed: Apr. 5, 2012

(86) PCT No.: PCT/US2012/032322
§ 371 (c)(1),
(2), (4) Date: Oct. 24, 2013

(87) PCT Pub. No.: WO2012/138858
PCT Pub. Date: Oct. 11, 2012

(65) Prior Publication Data
US 2014/0050709 A1 Feb. 20, 2014

Related U.S. Application Data

(60) Provisional application No. 61/473,457, filed on Apr. 8, 2011.

(51) Int. Cl.
*A01N 63/00* (2006.01)
*C12N 5/071* (2010.01)
*C12N 15/63* (2006.01)
*A61K 35/12* (2015.01)
*C12N 5/078* (2010.01)
*C12N 15/85* (2006.01)
*A61K 39/00* (2006.01)

(52) U.S. Cl.
CPC ............ *A61K 35/12* (2013.01); *C12N 5/0634* (2013.01); *C12N 15/85* (2013.01); *A61K 39/0011* (2013.01); *A61K 2039/5158* (2013.01); *C12N 15/63* (2013.01); *C12N 2501/2304* (2013.01); *C12N 2501/2307* (2013.01); *C12N 2510/00* (2013.01)

(58) Field of Classification Search
CPC ............... A61K 35/12; A61K 39/0011; A61K 2039/5158; C12N 15/63; C12N 2501/2304; C12N 2501/2307; C12N 2510/00
USPC .............................. 424/93.21; 435/372.3, 455
See application file for complete search history.

(56) References Cited

U.S. PATENT DOCUMENTS 5,747,292 A * 5/1998 Greenberg et al. .......... 435/69.7
7,235,392 B2 6/2007 Platz
7,371,570 B2 5/2008 Yu et al.
8,889,141 B2 11/2014 Stauss et al.
10,239,948 B2 3/2019 Juillerat et al.
2003/0171546 A1* 9/2003 Jensen
2015/0038684 A1 2/2015 Jensen

FOREIGN PATENT DOCUMENTS

| JP | 2001-501827 A | 2/2001 |
| JP | 2002-516562 A | 6/2002 |
| JP | 2004-531237 A | 10/2004 |
| WO | 1998/015616 A1 | 4/1998 |
| WO | 2002067862 A2 | 9/2002 |
| WO | 2004/019953 A1 | 3/2003 |

OTHER PUBLICATIONS

Taha, Masoumeh F., 2010, Current Stem Cell research & therapy, vol. 5, p. 23-36.*
Wu et al., 2012, Ageing Research Reviews, vol. 11, p. 32-40.*
Ikehara et al., 2013, Frontier in Cell and Developmental Biology, vol. 1, Article 2, p. 1-2.*
Sprangers et al., 2008, Kidney International, vol. 74, p. 14-21.*
Steinert et al., 2007, Arthritis Research & therapy, vol. 9, No. 3, 213, p. 1-15.*
Agrahari et al., 2017, Expert Opinion on Drug Delivery, vol. 14, No. 10, p. 1145-1162.*
Li et al., 2009, Transplant Immunology, vol. 21, p. 70-74.*
Vadori et al., 2014, Cold Spring Harbor Perspectives in Medicine, 4: a015578, p. 1-19.*
Vadori et al., 2015, Tissue Antigens, vol. 86, p. 239-253.*
Jena et al., "Redirecting T-cell specificity by introducing a tumor-specific chimeric antigen receptor", Blood, Apr. 19, 2010 (published online May 3, 2010, vol. 116, No. 7, pp. 1035-1044.
Wilkie et al., "Selective Expansion of Cimeric Anitgen Receptor-targeted T-cells with Ptent Effector Funcation using Interleukin-4", The Journal of Biological Chemistry, Aug. 13, 2010, vol. 285, No. 33, pp. 25538-25544.
International Search Report and Written Opinion dated Jul. 2, 2012, during examination of International Application No. PCT/US12/32322.
Parente-Pereira et al. "Trafficking of CAR-Engineered Human T Cells Following Regional or Systemic Adoptive Transfer in SCID Beige Mice" J. Clin. Immunol., Apr. 20, 2011, vol. 31, No. 4, pp. 710-718; Kluwer Academic Publishers-Plenum Pubishers, NE.
Leen et al. "Reversal of Tumor Immune Inhibition Using a Chimeric Cytokine Receptor", Molecular Therapy, Jun. 2014, vol. 22, No. 6, pp. 1211-1220.

(Continued)

*Primary Examiner* — Shin Lin Chen
(74) *Attorney, Agent, or Firm* — Norton Rose Fulbright US LLP

(57) ABSTRACT

Disclosed are compositions and methods related to rendering ineffective Th1 T cells resistant to the inhibitory cytokine milieu present in a cancer microenvironment. Tumor-specific T cells are modified to employ a chimeric receptor that binds inhibitory/suppressive cytokines and converts their intracellular consequences to a Th1 immunostimulatory/activating signal. The T cells employ a chimeric antigen receptor having exodomains for IL10, IL13 and/or IL4 fused with the signal transducing endodomains for IL2 and/or IL7.

6 Claims, 17 Drawing Sheets

(56) References Cited

OTHER PUBLICATIONS

International Preliminary Report on Patentability dated Oct. 8, 2013, during examination of International Application No. PCT/US2012/032322.

Zhu, Hui, et al; Physiologically Based Kinetic Model of Effector Cell Biodistribution in Mammals: Implications for Adoptive Immunotherapy;American Association of Cancer Research 56, 3771-3781, Aug. 15, 1996.

Clemons-Miller, Annette R., et al: Intrathecal Cytotoxic T-Cell Immunotherapy for Metastatic Leptomeningeal Melanoma; American Assocation for Cancer Research; vol. 7, 917s-924s; Mar. 2011 (Suppl.).

Zhong, Xiao-Song, et al; Chimeric Antigen Receptors Combining 4-1BB and CD28 Signaling Domains Augment PI3Kinase/AKT/Bcl-XL Activation and CD8+ T-Cell-mediated Tumor Eradication; Molecular Therapy, vol. 18, No. 2,413-420; Feb. 2010.

Zhao, Yangbing, et al; A Herceptin-Based Chimeric Antigen Receptor with Modified Signaling Domains Leads to Enhanced Survival of Transduced T Lymphocytes and Antitumor Activity; Journal of Immunology; Oct. 21, 2015.

Liu, David, L., et al; Immunotherapy in Liver Tumors: III. A New Experimental Model of Metastatic Liver Tumors from Colorectal Carcinoma for Cytokine Therapy; Cancer Letters 88 (1995) 211-219.

Von Beust, Barbara R., et al; Improving the Therapeutic Index of CpG Oligodeoxynucleotides by Intralymphatic Administraion; Eur. J. Immunol. 2005. 35; 1869-1876.

Yamasaki, Kazuki, et al; Induction of NKT Cell-Specific Immune Responses in Cancer Tissues After NKT Cell-Targeted Adoptive Immunotherapy; Clinical Immunology (2011) 138, 255-265.

Mihara, Keichiro, et al; Synergistic and Persistent Effect of T-Cell Immunotherapy with ANti-CD19 or anti-CD38 Chimeric Receptor in Conjunction with Rituximab on B-Cell non-Hodgkin Lymphoma; British Journal of Haematology; Jul. 2010; 151, 37-46.

Sadelain, Michel, et al; The Promis and Potential Pitfalls of Chimeric Antigen Receptors; Science Direct, Current Opinion in Immunology 2009, 21:215-223.

Li, L, et al; Expression of Chimeric ANtigen Receptors in Natural Killer vcells with a Regulatory-Compliant Non-Viral Method; Cancer Gene Therapy (2009), 1-8.

Amara et al., "Prostate Stem Cell Antigen is Overexpressed in Human Transitional Cell Carcinoma," *Cancer Research*, 61:4660-4665, (2001).

Argani et al., "Discovery of New Markers of Cancer through Serial Analysis of Gene Expression:" Prostate Stem Cell Antigen is Overexpressed in Pancreatic Adenocarcinoma, *Cancer Research*, 61:4320-4324, (2001).

Caballero et al., "Cancer/testis (CT) antigens: Potential targets for immunotherapy," *Cancer Science*, 100(11): 2014-2021, (2009).

Elsamman et al., "The expression of prostate stem cell antigen in human clear cell renal cell carcinoma: a quantitative reverse transcriptase-polymerase chain reaction analysis," *BJU International*, 98:668-673, (2006).

Geiger et al., "The prostate stem cell antigen represents a novel glioma-associated antigen," *Oncology Reports*, 26:13-21, (2011).

Kim et al., "The clinical significance of MAGEA3 expression in pancreatic cancer," *Int. J. Cancer*, 118:2269-2275, (2006).

Mohammed et al., "Improving Chimeric Antigen Receptor-Modified T Cell Function by Reversing the Immunosuppressive Tumor Microenvironment of Pancreatic Cancer," *Molecular Therapy*, 25(1):249-258, (2017).

Otte et al., "MAGE-A Gene Expression Pattern in Primary Breast Cancer," *Cancer Research*, 61:6682-6687, (2001).

Petersen et al., "Accumulation in Tumor Tissue of Adoptively Transferred T Cells: a Comparison Between Intravenous and Intraperitoneal Injection," J Immunother, 29(3): 241249, (2006).

Sienel et al., "Melanoma associated antigen (Mage)-A3 expression in Stages I and Ii nonsmall cell lung cancer: results of a multi-center study," European Journal of Cardio-thoracic Surgery, 25:131-134, (2004).

C11 Smith et al., "The Ssx Family of Cancer-Testis Antigens as Target Proteins for Tumor Therapy," Clinical and Developmental Immunology, 2010: 150591, (2010).

Tsuneyama et al., "Expression of Mage-A3 in intrahepatic cholangiocarcinoma and its precursor lesions," Pathology International, 54:181-186, (2004).

Honjo, Eijiro, et al: "Preparation and Characterization of Extracellular Region of Interleukin-13 Receptor al and Interleukin-4 receptor a "; Abstract Poster 4P-0310.

* cited by examiner

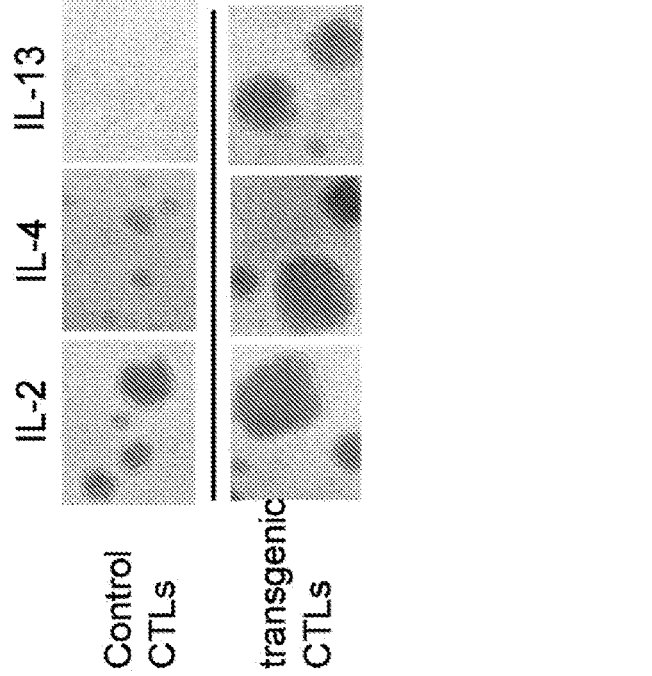

REVERSING THE EFFECTS OF THE TUMOR MICROENVIRONMENT USING CHIMERIC CYTOKINE RECEPTORS

This application is a national phase application under 35 U.S.C. § 371 that claims priority to International Application No. PCT/US2012/032322 filed Apr. 5, 2012 which claims priority to U.S. Provisional Patent Application Ser. No. 61/473,457, filed Apr. 8, 2011, both of which are incorporated by reference herein in their entirety.

TECHNICAL FIELD

The field of the invention at least generally includes the fields of immunology, cell biology, molecular biology, and medicine.

BACKGROUND OF THE INVENTION

Conventional chemo and radiotherapy often produce insufficient benefit, underscoring the need for novel therapeutics. The adoptive transfer of in vitro expanded tumor-associated antigen (TAA)-specific cytotoxic T lymphocytes (CTL) can effectively treat tumors including Hodgkin's Lymphoma, nasopharyngeal carcinoma, neuroblastoma and melanoma, for example. While the infusion of CTLs targeting cancer-expressed TAA is useful therapeutically, at least some tumors use multiple mechanisms of immune evasion, including downregulation of antigen expression, and the release of soluble immunomodulatory cytokines, such as IL13 and IL4, that favor development of a Th2 rather than a cytotoxic Th1 type immune response. The present invention provides a solution to a need in the art to facilitate overcoming such evasive measures by the tumor.

BRIEF SUMMARY OF THE INVENTION

Progressive tumor growth may be associated with suppression of the immune response. Many different mechanisms may contribute to immune evasion, however many types of cancers have taken advantage of the regulatory role of cytokines to down-regulate appropriate immune responses targeted at destroying cancer cells. They do this by secreting immunosuppressive cytokines that serve to recruit regulatory immune cells to the tumor and directly inhibit and/or re-polarize cytotoxic Th1 T cells to an ineffective Th2 phenotype. Immunosuppressive cytokines secreted by cancer cells or the surrounding tumor stroma include at least interleukin (IL) 13, IL4, (transforming growth factor-beta) TGF-beta, IL6, IL8, and IL-10.

Embodiments of the invention provide a novel approach to render tumor-reactive T cells resistant to the immunosuppressive/inhibitory cytokines present in the tumor microenvironment. Certain embodiments of the invention concern improved expansion and anti-tumor activity of tumor-specific CTLs using a transgenic chimeric cytokine receptor.

Embodiments of the invention provide a novel approach to render effector Th1 T cells resistant to the inhibitory cytokine milieu present in the tumor microenvironment. Such embodiments encompass native or genetically modified tumor-specific T cells with a chimeric receptor that binds inhibitory/suppressive cytokines and converts their intracellular consequences to a Th1 immunostimulatory/activating signal, thus improving the efficacy of tumor-specific T cells.

By example, the invention encompasses vectors, such as exemplary bicistronic retroviral vectors, that encode the exodomains for IL4 and/or IL13 cytokine receptors fused with the signal transducing endodomains for 1L2 and/or IL7 cytokine receptors. Similarly, the invention encompasses a vector, such as a retroviral vector, that encodes the exodomains of the IL10 cytokine receptor fused with the signal transducing endodomains for IL2 and/or IL1 cytokine receptors.

In specific embodiments, cancers wherein one or more of IL13, IL4 and/or IL10 (or others) are present in the microenvironment include essentially all solid tumors. Particular exemplary cancers include at least: pancreatic cancer, Hodgkin's and non-Hodgkin's lymphoma, melanoma, breast cancer, lung cancer, prostate cancer, glioblastoma, hepatocellular carcinoma, ovarian cancer, and so forth.

Embodiments of the invention are useful to modify primary T cells, naturally occurring tumor antigen-specific cytotoxic T lymphocytes, and NK cells, for example. T/NK cells modified using this invention can be used in an autologous or allogeneic setting.

In some embodiments of the invention, there are chimeric molecules that can convert negative immunoregulatory signals to positive signals. This approach involves, by way of example only, fusing the exodomains of IL-4 and/or IL-13 with the signal transducing endodomains of the IL-2 and/or IL-7 receptors. This approach can be used to render effector Th1 cells resistant to negative cytokine signals that often present in the tumor microenvironment.

In some embodiments, the present invention provides reversing the effects of the tumor microenvironment using chimeric cytokine receptors: exodomains of IL-4 and/or IL-13 fused with the endodomains of IL-2 and/or IL-7 receptors.

In specific embodiments, the present invention allows reversing the effects of the tumor microenvironment using chimeric cytokine receptors: exodomains of IL-4 and IL-13 fused with the endodomains of IL-2 and IL-7 receptors, for example.

In some embodiments of the invention, there is a method of preventing inhibition or re-polarization of cytotoxic Th1 T cells to cells having a Th2 phenotype, comprising the step of modifying tumor-specific T cells to comprise a chimeric receptor that binds inhibitory or suppressive cytokines, wherein upon binding to the chimeric receptor by the inhibitory or suppressive cytokines the inhibition or re-polarization of cytotoxic Th1 T cells is thereby prevented. In specific embodiments, the chimeric receptor comprises the exodomain of the IL10, IL4, and/or IL13 cytokine receptor(s) and comprises the signal transducing endodomain of the IL2 and/or IL7 cytokine receptor(s). In certain embodiments, the chimeric receptor comprises the exodomain of an immunosuppressive cytokine and the endodomain of cytokines that transmit Th1 signals.

In some embodiments, there is a vector, comprising a chimeric receptor that comprises the exodomain of an immunosuppressive cytokine receptor and the endodomain of a cytokine receptor that transmits Th1 signals. In some embodiments, the exodomain of an immunosuppressive cytokine is an exodomain of IL10, IL4, and/or IL13 cytokine receptor. In certain embodiments, the endodomain of a cytokine receptor that transmits Th1 signals is an endodomain of a cytokine receptor for the IL2 and/or IL7 cytokine receptors. The vector may be of any kind, including a retroviral vector, an adenoviral vector, a plasmid, or an adeno-associated viral vector. In specific embodiments, the chimeric receptor comprises the exodomain of IL4 and the endodomain of IL7.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIGS. 2A-2D. FIG. 2A) Vector map of exemplary constructs #1 and #2. FIG. 2B) evaluating transduction efficiency by GFP (#1) and mOrange (#2) expression; FIG. 2C) Phospho Stat5 after 10 min cytokine exposure; FIG. 2D) transduced and control CTLs cultured in IL2, 4, or 13.

DETAILED DESCRIPTION OF EMBODIMENTS OF THE INVENTION

I. Definitions

Figure 1:
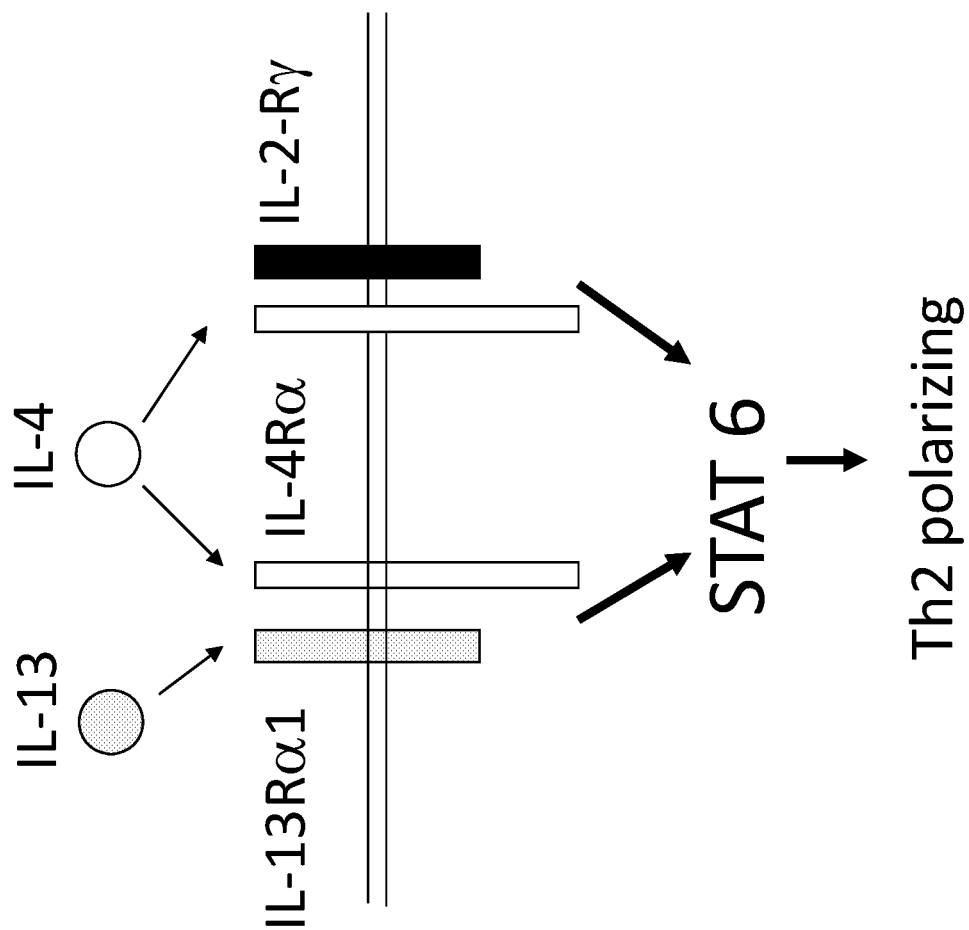
FIG. 1. Schematic of IL4 and IL13 signaling.

As used herein in the specification, "a" or "an" may mean one or more. As used herein in the claim(s), in conjunction with the word "comprising," the words "a" or "an" may mean one or more than one. As used herein "another" may mean at least a second or more of an item.

The term "chimeric cytokine receptor" as used herein refers to an engineered receptor comprising cytokine binding portion from one receptor linked to intracellular signalling portion from a different receptor.

The term "cytokine-binding exodomain" as used herein refers to the portion of a cytokine receptor on the cell surface that binds to a cytokine.

The term "signal transducing endodomain" as used herein refers to the portion of a cytokine receptor within the cells that is responsible for transmitting a signal upon cytokine binding.

II. General Embodiments of the Invention

To overcome barriers in the art and develop an effective immunotherapeutic strategy against cancer, embodiments of the invention encompass CTL lines (T cell lines with native tumor specificity) or chimeric antigen receptor (CAR)-modified T cells that target antigens expressed on malignant cells, and engineering of these cells to express chimeric receptors containing the cytokine-binding exodomains of the IL13 receptor α (IL13Rα1) and the IL4Rα linked to the endodomains of the IL2Rγ and IL7Rα, which transmit Th1 signals. In specific embodiments, these manipulations render CTL resistant to the Th2-polarizing tumor microenvironment and instead sustain Th1 signaling to the CTLs targeted to TAA. One can examine cancer patient samples and document the pattern of TAA expression and the levels and pattern of Th2 cytokines produced. One can then determine whether CTLs can be expanded that are directed against the expressed antigens from patient PBMC and characterize the effects of modifying them so that they remain polarized to Th1 activity even in the Th2inducing tumor microenvironment. In specific embodiments, T cells reactive against pancreatic cancer-associated antigens (by example only) can be generated from patient PBMC and modified to retain Th1 function even in the Th2 cytokine milieu of the tumor. Such embodiments can be examined as follows: 1) document the pattern of TAA expression and assess the cytokine profile of primary biopsy samples; 2) generate tumor-reactive CTL specific for multiple pancreatic cancer-associated target antigens and evaluate their specificity and function in vitro; and 3) protect CTLs from the inhibitory effects of signaling with Th2 cytokines by forced expression of chimeric cytokine receptors. Following this, one can evaluate the safety and anti-tumor efficacy of TAA-CTL in individuals with cancer, including pancreatic cancer.

Survival and expansion of tumor-specific CTLs is important for optimal in vivo efficacy of T cell therapies. Although IL2 administration may produce these effects, it is associated with toxicity and expansion of inhibitory T cell populations that limit benefit. Transgenic expression of the IL7 receptor can improve CTL survival and expansion, but is of benefit only with repeated exogenous administration of IL7 cytokine, which is expensive, relies on the availability of clinical grade product, and which may be at inadequate concentrations at the tumor site. Embodiments of the present invention provide manipulated T cell responses to IL4, a cytokine that is endogenously present in abundance in the microenvironment of several tumors and is otherwise associated with pro-tumorigenic actions including cancer cell proliferation, protection of tumor cells from apoptosis and repolarization of cytotoxic tumor-specific T cells to a suppressive Th2 phenotype. To reverse the inhibitory effects of IL4 on tumor-specific CTLs and instead enable them to utilize IL4 as a growth factor, the inventors engineered a retroviral vector encoding the IL4Rα exodomain (cytokine-binding portion) fused with the endodomain (signaling domain) of the IL7R and linked with mOrange to allow transgene detection. To determine whether transgenic expression of chimeric IL4/7R improves CTL survival and expansion the inventors used killing of Epstein Barr virus+ (EBV+) tumor by EBV-specific CTLs. After transduction, IL4/7R CTLs were detectable by flow cytometry (double positive mOrange, IL4R) in 13-76% of EBV-CTLs. The transgenic molecule was functional since addition of IL4 phosphorylated STAT5 only in EBV-CTLs/IL4/7R+ at levels similar to that achieved after IL2 administration. Both transgenic and control CTLs expanded in response to IL2 (increase from $1\times10^6$ to $3.5\times10^7$ and $5.3\times10^7$ cells, respectively), but only EBV-CTL/IL4/7R+ expanded in the presence of IL4 (1000 Ulml) (from $1\times10^6$ to $2.9\times10^7$ vs. $3.2\times10^6$ CTLs, respectively) over 1 week. As anticipated, the transgenic subpopulation of EBV-CTL were positively selected in the presence of IL4 (increase from 13% to 80% in 1 week) compared to CTL cultured in IL2. Following expansion with IL4, transgenic CTL remained polyclonal, with an effector-memory profile, and retained antigen specificity measured by IFNγ release, EBV-pentamer binding, and MHC-restricted killing of autologous EBV-LCLs. Importantly, CTL expansion remained strictly antigen and cytokine dependent, as withdrawal of either stimulus terminated expansion. These in vitro characteristics were replicated in vivo in a xenograft mouse model in which EBV-CTLs/IL4/7R expanded in response to IL2 or IL4 and maintained their anti-EBV-tumor activity. Finally, CTLs were cultured in the presence of supernatant harvested from IL-4-producing tumors. Only the transgenic CTL depleted the cytokine from the media. Hence, in embodiments of the invention IL4/7R CTL are able to utilize tumor-derived IL4 as a growth factor and serve as a sink that depletes the cytokine from the tumor microenvironment, thus starving the malignancy of a protein that would otherwise benefit tumor growth and survival.

III. Tumor Associated Antigens

In embodiments wherein multiTAA-specific CTL are employed for the treatment and/or prevention of cancer, a variety of TAA may be targeted. Tumor antigens are substances produced in tumor cells that trigger an immune response in a host.

Exemplary tumor antigens include at least the following: carcinoembryonic antigen (CEA) for bowel cancers; CA-125 for ovarian cancer; MUC-1 or epithelial tumor antigen (ETA) or CA15-3 for breast cancer; tyrosinase or melanoma-associated antigen (MAGE) for malignant melanoma; and abnormal products of ras, p53 for a variety of types of tumors; alphafetoprotein for hepatoma, ovarian, or testicular cancer; beta subunit of hCG for men with testicular cancer; prostate specific antigen for prostate cancer; beta 2 microglobulin for multiple myelom and in some lymphomas; CA19-9 for colorectal, bile duct, and pancreatic cancer; chromogranin A for lung and prostate cancer; TA90, GP100, and MelanA/MART1 for melanoma, soft tissue sarcomas, and breast, colon, and lung cancer. Examples of tumor antigens are known in the art, for example in Cheever et al., 2009, which is incorporated by reference herein in its entirety.

Specific examples of tumor antigens include at least CEA, MHC, CTLA-4, gp100, mesothelin, PD-L1, TRP1, CD40, EGFP, Her2, TCR alpha, trp2, TCR, MUC1, cdr2, ras, 4-1BB, CT26, GITR, OX40, TGF-α. WT1, MUC1, LMP2, HPV E6 E7, EGFRvIII, HER-2/neu, MAGE A3, p53 non-mutant, NY-ESO-1, PSMA, GD2, Melan A/MART1, Ras mutant, gp 100, p53 mutant, Proteinase3 (PR1), bcr-abl, Tyrosinase, Survivin, PSA, hTERT, EphA2, PAP, ML-IAP, AFP, EpCAM, ERG (TMPRSS2 ETS fusion gene), NA17, PAX3, ALK, Androgen receptor, Cyclin B1, Polysialic acid, MYCN, RhoC, TRP-2, GD3, Fucosyl GM1, Mesothelin, PSCA, MAGE A1, sLe(a), CYP1B1, PLAC1, GM3, BORIS, Tn, GloboH, ETV6-AML, NY-BR-1, RGSS, SART3, STn, Carbonic anhydrase IX, PAXS, OY-TES1, Sperm protein 17, LCK, HMWMAA, AKAP-4, SSX2, XAGE 1, B7H3, Legumain, Tie 2, Page4, VEGFR2, MAD-CT-1, FAP, PDGFR-β, MAD-CT-2, and Fos-related antigen 1, for example.

IV. Nucleic Acids

Nucleic acids according to the present invention may encode a chimeric cytokine receptor. The nucleic acid may be derived from genomic DNA, complementary DNA (cDNA) or synthetic DNA.

A "nucleic acid" as used herein includes single-stranded and double-stranded molecules, as well as DNA, RNA, chemically modified nucleic acids and nucleic acid analogs. It is contemplated that a nucleic acid within the scope of the present invention may be of almost any size, determined in part by the length of the encoded protein or peptide.

It is contemplated that chimeric cytokine receptors may be encoded by any nucleic acid sequence that encodes the appropriate amino acid sequence. The design and production of nucleic acids encoding a desired amino acid sequence is well known to those of skill in the art, using standardized codon tables. In preferred embodiments, the codons selected for encoding each amino acid may be modified to optimize expression of the nucleic acid in the host cell of interest.

V. Targeted Delivery of Gene Therapy Vectors

In particular embodiments of the invention, vectors are employed that allow integration rather than transient expression, such as retrovirus, lentivirus, and transposons.

There are a number of ways in which gene therapy vectors may introduced into cells. In certain embodiments of the invention, the gene therapy vector comprises a virus. The ability of certain viruses to enter cells via receptor-mediated endocytosis, to integrate into host cell genome or be maintained episomally, and express viral genes stably and efficiently have made them attractive candidates for the transfer of foreign genes into mammalian cells (Ridgeway, 1988; Nicolas and Rubinstein, 1988.; Baichwal and Sugden, 1986; Temin, 1986). Preferred gene therapy vectors are generally viral vectors. DNA viruses used as gene therapy vectors include the papovaviruses (e.g., simian virus 40, bovine papilloma virus, and polyoma) (Ridgeway, 1988; Baichwal and Sugden, 1986) and adenoviruses (Ridgeway, 1988; Baichwal and Sugden, 1986).

Other gene transfer vectors may be constructed from retroviruses. (Coffin, 1990.) In order to construct a retroviral vector, a nucleic acid encoding protein of interest is inserted into the viral genome in the place of certain viral sequences to produce a virus that is replication-defective. In order to produce virions, a packaging cell line containing the gag, pol, and env genes, but without the LTR and packaging components, is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are capable of infecting a broad variety of cell types. However, integration and stable expression require the division of host cells (Paskind et al., 1975).

Other viral vectors may be employed as targeted gene therapy vectors. Vectors derived from viruses such as vaccinia virus (Ridgeway, 1988; Baichwal and Sugden, 1986; Coupar et al., 1988), adeno-associated virus (AAV) (Ridgeway, 1988; Baichwal and Sugden, 1986; Hermonat and Muzycska, 1984), and herpes viruses may be employed.

In a further embodiment of the invention, gene therapy construct may be entrapped in a liposome. Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa, and hepatoma cells. Nicolau et al., (1987.) accomplished successful liposome-mediated gene transfer in rats after intravenous injection.

Gene therapy vectors of the invention may comprise various transgenes, which are typically encoded DNA or RNA of an expression vector. Gene therapy may be used for the expression of a therapeutic gene, expression of APA to enhance neo-vascularization or for the inhibition of APA expression for the treatment of disease states associated with neo-vascularization. DNA may be in form of cDNA, in vitro polymerized DNA, plasmid DNA, parts of a plasmid DNA, genetic material derived from a virus, linear DNA, vectors (P1, PAC, BAC, YAC, artificial chromosomes), expression cassettes, chimeric sequences, recombinant DNA, chromosomal DNA, an oligonucleotide, anti-sense DNA, or derivatives of these groups. RNA may be in the form of oligonucleotide RNA, tRNA (transfer RNA), snRNA (small nuclear RNA), rRNA (ribosomal RNA), mRNA (messenger RNA), in vitro polymerized RNA, recombinant RNA, chimeric sequences, anti-sense RNA, siRNA (small interfering RNA), ribozymes, or derivatives of these groups. An antisense polynucleotide is a polynucleotide that interferes with the function of DNA and/or RNA. Antisense polynucleotides include, but are not limited to: morpholinos, 2'-O-methyl polynucleotides, DNA, RNA and the like. SiRNA comprises a double stranded structure typically containing 15-50 base pairs and preferably 21-25 base pairs and having a nucleotide sequence identical or nearly identical to an expressed target gene or RNA within the cell. Interference may result in suppression of expression. The polynucleotide can also be a sequence whose presence or expression in a cell alters the expression or function of cellular genes or RNA, e.g., APA. In addition, DNA and RNA may be single, double, triple, or quadruple stranded.

VI. Pharmaceutical Compositions

Pharmaceutical compositions of the present invention comprise an effective amount of one or more compositions including a vector or a cell harboring a vector wherein the vector encodes a chimeric cytokine receptor of the invention, as described herein, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one composition of the present invention or an additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The therapeutic and diagnostic compositions of the present invention may comprise different types of carriers depending on whether it is to be administered in solid, liquid or aerosol form, and whether it need to be sterile for such routes of administration. The present invention can be administered intravenously, intradermally, intraarterially, intraperitoneally, intralesionally, intracranially, intraarticularly, intrapleurally, intratracheally, intratumorally, intramuscularly, intraperitoneally, subcutaneously, intravesicularlly, sublingually, by inhalation (e.g. aerosol inhalation), injection, infusion, continuous infusion, localized perfusion bathing target cells directly, via a catheter, via a lavage, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to a subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 μg/kg/body weight, about 5 μg/kg/body weight, about 10 μg/kg/body weight, about 50 μg/kg/body weight, about 100 μg/kg/body weight, about 200 μg/kg/body weight, about 350 μg/kg/body weight, about 500 μg/kg/body weight, about 1 mg/kg/body weight, about 5 mg/kg/body weight, about 10 mg/kg/body weight, about 50 mg/kg/body weight, about 100 mg/kg/body weight, about 200 mg/kg/body weight, about 350 mg/kg/body weight, about 500 mg/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In embodiments where the composition is in a liquid form, a carrier can be a solvent or dispersion medium comprising but not limited to, water, ethanol, polyol (e.g., glycerol, propylene glycol, liquid polyethylene glycol), lipids (e.g., triglycerides, vegetable oils, liposomes) and combinations thereof. In many cases, it will be preferable to include isotonic agents, such as, for example, sugars, sodium chloride or combinations thereof.

Sterile injectable solutions are prepared by incorporating the APA targeting moiety or conjugate thereof in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

VII. Combination Therapy

In certain embodiments of the invention, methods of the present invention for clinical aspects are combined with other agents effective in the treatment of hyperproliferative disease, such as anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cancer cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

Tumor cell resistance to chemotherapy and radiotherapy agents represents a major problem in clinical oncology. One goal of current cancer research is to find ways to improve the efficacy of chemo- and radiotherapy by combining it with gene therapy. For example, the herpes simplex-thymidine kinase (HS-tK) gene, when delivered to brain tumors by a retroviral vector system, successfully induced susceptibility to the antiviral agent ganciclovir (Culver, et al., 1992). In the context of the present invention, it is contemplated that cell therapy could be used similarly in conjunction with chemotherapeutic, radiotherapeutic, or immunotherapeutic intervention, in addition to other pro-apoptotic or cell cycle regulating agents.

Alternatively, the present inventive therapy may precede or follow the other agent treatment by intervals ranging from minutes to weeks. In embodiments where the other agent and present invention are applied separately to the individual, one would generally ensure that a significant period of time did not expire between the time of each delivery, such that the agent and inventive therapy would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, present invention is "A" and the secondary agent, such as radio- or chemotherapy, is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

It is expected that the treatment cycles would be repeated as necessary. It also is contemplated that various standard therapies, as well as surgical intervention, may be applied in combination with the inventive cell therapy.

A. Chemotherapy

Cancer therapies also include a variety of combination therapies with both chemical and radiation based treatments. Combination chemotherapies include, for example, abraxane, altretamine, docetaxel, herceptin, methotrexate, novantrone, zoladex, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing.

B. Radiotherapy

Other factors that cause DNA damage and have been used extensively include what are commonly known as y-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

C. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with the present cell therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

D. Genes

In yet another embodiment, the secondary treatment is a gene therapy in which a therapeutic polynucleotide is administered before, after, or at the same time as the present invention clinical embodiments. A variety of expression products are encompassed within the invention, including inducers of cellular proliferation, inhibitors of cellular proliferation, or regulators of programmed cell death.

E. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

F. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

DNA methyltransferase inhibitors and/or histone deacetylase inhibitors. Exemplary DNA methyltransferase inhibitors include, for example, 5-azacytidine, 5-aza-2'-deoxycytidine, 1-beta-D-arabinofuranosyl-5-azacytosine and dihydro-5-azacytidine. Exemplary HDAC inhibitors include hydroxamic acids, such as trichostatin A; cyclic tetrapeptides (such as trapoxin B), and the depsipeptides; benzamides; electrophilic ketones; and the aliphatic acid compounds such as phenylbutyrate and valproic acid.

G. Regulators of Programmed Cell Death

Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins that share in common structural and sequence homologies. These different family members have been shown to either possess similar functions to Bcl-2 (e.g., $Bcl_{XL}$, $Bcl_W$, $Bcl_S$, Mcl-1, A1, Bfl-1) or counteract Bcl-2 function and promote cell death (e.g., Bax, Bak, Bik, Bim, Bid, Bad, Harakiri).

H. Angiogenic Inhibitors

In certain embodiments the present invention may concern administration of targeting moieties operatively coupled to anti-angiogenic agents, such as angiotensin, laminin peptides, fibronectin peptides, plasminogen activator inhibitors, tissue metalloproteinase inhibitors, interferons, interleukin 12, platelet factor 4, IP-10, Gro-β, thrombospondin, 2-methoxyoestradiol, proliferin-related protein, carboxiamidotriazole, CM101, Marimastat, pentosan polysulphate, angiopoietin 2 (Regeneron), interferon-alpha, herbimycin A, PNU145156E, 16K prolactin fragment, Linomide, thalidomide, pentoxifylline, genistein, TNP-470, endostatin, paclitaxel, accutin, angiostatin, cidofovir, vincristine, bleomycin, AGM-1470, platelet factor 4 or minocycline.

Proliferation of tumors cells relies heavily on extensive tumor vascularization, which accompanies cancer progression. Thus, inhibition of new blood vessel formation with anti-angiogenic agents and targeted destruction of existing blood vessels have been introduced as an effective and relatively non-toxic approach to tumor treatment. (Arap et al., 1998; Arap et al., 1998; Ellerby et al., 1999). A variety of anti-angiogenic agents and/or blood vessel inhibitors are known. (e.g., Folkman, 1997; Eliceiri and Cheresh, 2001).

I. Cytotoxic Agents

Chemotherapeutic (cytotoxic) agents may be used to treat various disease states, including cancer. Chemotherapeutic (cytotoxic) agents of potential use include, but are not limited to, 5-fluorouracil, bleomycin, busulfan, camptothecin, carboplatin, chlorambucil, cisplatin (CDDP), cyclophosphamide, dactinomycin, daunorubicin, doxorubicin, estrogen receptor binding agents, etoposide (VP16), farnesyl-protein transferase inhibitors, gemcitabine, ifosfamide, mechlorethamine, melphalan, mitomycin, navelbine, nitrosurea, plicomycin, procarbazine, raloxifene, tamoxifen, taxol, temazolomide (an aqueous form of DTIC), transplatinum, vinblastine and methotrexate, vincristine, or any analog or derivative variant of the foregoing. Most chemotherapeutic agents fall into the categories of alkylating agents, antimetabolites, antitumor antibiotics, corticosteroid hormones, mitotic inhibitors, and nitrosoureas, hormone agents, miscellaneous agents, and any analog or derivative variant thereof.

Chemotherapeutic agents and methods of administration, dosages, etc. are well known to those of skill in the art (see for example, the "Physicians Desk Reference", Goodman & Gilman's "The Pharmacological Basis of Therapeutics" and in "Remington's Pharmaceutical Sciences" $15^{th}$ ed., pp 1035-1038 and 1570-1580, incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject. Of course, all dosages and agents described herein are exemplary rather than limiting, and other doses or agents may be used by a skilled artisan for a specific patient or application. Any dosage in-between these points, or range derivable therein is also expected to be of use in the invention.

J. Alkylating Agents

Alkylating agents are drugs that directly interact with genomic DNA to prevent cells from proliferating. This category of chemotherapeutic drugs represents agents that affect all phases of the cell cycle, that is, they are not phase-specific. An alkylating agent, may include, but is not limited to, a nitrogen mustard, an ethylenimene, a methylmelamine, an alkyl sulfonate, a nitrosourea or a triazines. They include but are not limited to: busulfan, chlorambucil, cisplatin, cyclophosphamide (cytoxan), dacarbazine, ifosfamide, mechlorethamine (mustargen), and melphalan.

K. Antimetabolites

Antimetabolites disrupt DNA and RNA synthesis. Unlike alkylating agents, they specifically influence the cell cycle during S phase. Antimetabolites can be differentiated into various categories, such as folic acid analogs, pyrimidine analogs and purine analogs and related inhibitory compounds. Antimetabolites include but are not limited to, 5-fluorouracil (5-FU), cytarabine (Ara-C), fludarabine, gemcitabine, and methotrexate.

L. Natural Products

Natural products generally refer to compounds originally isolated from a natural source, and identified as having a pharmacological activity. Such compounds, analogs and derivatives thereof may be, isolated from a natural source, chemically synthesized or recombinantly produced by any technique known to those of skill in the art. Natural products include such categories as mitotic inhibitors, antitumor antibiotics, enzymes and biological response modifiers.

Mitotic inhibitors include plant alkaloids and other natural agents that can inhibit either protein synthesis required for cell division or mitosis. They operate during a specific phase during the cell cycle. Mitotic inhibitors include, for example, docetaxel, etoposide (VP16), teniposide, paclitaxel, taxol, vinblastine, vincristine, and vinorelbine.

Taxoids are a class of related compounds isolated from the bark of the ash tree, *Taxus brevifolia*. Taxoids include but are not limited to compounds such as docetaxel and paclitaxel. Paclitaxel binds to tubulin (at a site distinct from that used by the vinca alkaloids) and promotes the assembly of microtubules.

Vinca alkaloids are a type of plant alkaloid identified to have pharmaceutical activity. They include such compounds as vinblastine (VLB) and vincristine.

M. Antibiotics

Certain antibiotics have both antimicrobial and cytotoxic activity. These drugs also interfere with DNA by chemically inhibiting enzymes and mitosis or altering cellular membranes. These agents are not phase specific so they work in all phases of the cell cycle. Examples of cytotoxic antibiotics include, but are not limited to, bleomycin, dactinomycin, daunorubicin, doxorubicin (Adriamycin), plicamycin (mithramycin) and idarubicin.

N. Miscellaneous Agents

Miscellaneous cytotoxic agents that do not fall into the previous categories include, but are not limited to, platinum coordination complexes, anthracenediones, substituted ureas, methyl hydrazine derivatives, amsacrine, L-asparaginase, and tretinoin. Platinum coordination complexes include such compounds as carboplatin and cisplatin (cis-DDP). An exemplary anthracenedione is mitoxantrone. An exemplary substituted urea is hydroxyurea. An exemplary methyl hydrazine derivative is procarbazine (N-methylhydrazine, MIH). These examples are not limiting and it is contemplated that any known cytotoxic, cytostatic or cytocidal agent may be attached to targeting peptides and administered to a targeted organ, tissue or cell type within the scope of the invention.

VIII. Kits of the Invention

Any of the compositions described herein may be comprised in a kit. In a non-limiting example modified cells comprising the chimeric cytokine receptors and/or reagents to generate such cells may be comprised in a kit. Such reagents include one or more of cells, nucleic acid vectors, buffers, nucleotides, oligonucleotides, and so forth. The kits will comprise any of its components in one or more suitable containers.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one components in the kit, the kit also will generally contain a second, third or other additional container into which the additional components may be separately placed. However, various combinations of components may be comprised in a vial. The kits of the present invention also will typically include a means for containing the components in close confinement for commercial sale. Such containers may include injection or blow-molded plastic containers into which the desired vials are retained. The components of the kit may be provided as dried powder(s). When reagents and/or components are provided as a dry powder, the powder can be reconstituted by the addition of a suitable solvent. It is envisioned that the solvent may also be provided in another container means.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Reversing the Effects of the Tumor Microenvironment Using Chimeric Cytokine Receptors Pancreatic cancer remains the fourth commonest cause of cancer mortality in developed countries. Clinical manifestations develop late and the disease metastasizes early, and the incidence and mortality rates have remained almost identical for >50 years (Sweeney et al., 2009; Wong et al., 2009). Improved treatment strategies based on understanding of the disease biology are thus needed. Tumor-associated antigens (TAA) expressed by malignant cells can be immunogenic, and thus are potential targets for immune destruction (Tassi et al, 2008; Han et al., 2009; Rong et al., 2009; Li et al., 2008; Plate, 2007). The adoptive transfer of in vitro expanded TAA-specific cytotoxic T lymphocytes (CTLs) can effectively treat tumors including Hodgkin's Lymphoma and melanoma (Bollard et al., 2007; Morgan et al., 2006). While infusion of CTLs targeting pancreatic cancer-expressed TAA has therapeutic potential, these tumors use multiple mechanisms of immune evasion, including downregulation of antigen expression, and the release of soluble immunomodulatory cytokines and other substances that favor development of a Th2 rather than a cytotoxic Th1 type immune response (Leen et al., 2007; Selcean et al., 2009; Formentini et al., 2009; Kornmann et al., 1999; Prokopchuk et al., 2005; Seruga et al., 2008).

To overcome these barriers and develop an effective immunotherapeutic strategy against pancreatic cancer, embodiments of the invention concern generating CTL lines that target antigens expressed on malignant cells, and engineering these CTL to express chimeric molecules containing the cytokine-binding exodomains of the IL13 receptor α (IL13Rα1) and the IL4Rα linked to the endodomains of the IL2Rγ and IL7Rα, which transmit Th1 signals (Formentini et al., 2009; Prokopchuk et al., 2005). In specific embodiments of the invention, these manipulations render CTL resistant to the Th2-polarizing tumor microenvironment, and instead sustain Th1 signaling to the CTLs targeted to TAA (Vera et al., 2009). One can begin by examining biopsy and serum samples from cancer patients, such as pancreatic cancer patients, and document the pattern of TAA expression and the levels and pattern of Th2 cytokines produced. One can then determine whether one can expand CTLs directed against the expressed antigens from patient PBMC, and the effects of modifying them so that they remain polarized to Th1 activity even in the Th2-inducing tumor microenvironment. In embodiments of the invention, T cells reactive against pancreatic cancer-associated antigens can be generated from patient PBMC and modified to retain Th1 function even in the Th2 cytokine milieu of the tumor. Such embodiments can be characterized by three exemplary approaches: 1) document the pattern of TAA expression and assess the cytokine profile of primary biopsy samples; 2) generate tumor-reactive CTL specific for multiple pancreatic cancer-associated target antigens and evaluate their specificity and function in vitro; and 3) protect CTLs from the inhibitory effects of signaling with Th2 cytokines by forced expression of chimeric cytokine receptors.

Background and Significance

Pancreatic cancer. Pancreatic cancer causes an estimated 213,000 annual deaths worldwide (Wong et al., 2009). Surgical resection remains the only curative therapy, resulting in a 15-20% 5-yr survival rate, but this option is not available to the majority who are diagnosed with locally advanced or metastatic disease (Sweeney et al., 2009; Tanis et al., 2009). Conventional chemotherapy and radiotherapy seldom produce substantive benefit, underscoring the need for novel therapeutics.

Adoptive immunotherapy for virus-associated malignancies. The inventors have routinely generated virus-specific CTL for adoptive transfer (Leen et al., 2006; Leen et al., 2009) and studies in >100 stem cell recipients have shown that donor-derived EBV-CTLs can safely protect patients against EBV-driven lymphomas and cure patients even with bulky established disease (Heslop et al., 2009; Heslop et al., 1996; Rooney et al., 1995). This approach has also shown success in the treatment of EBV+ve tumors in immunocompetent individuals (Bolard et al., 2007; Louis et al., 2009; Straathof et al., 2005; Bollard et al., 2004). In a recent phase I trial, 9/10 patients treated in remission of high-risk EBV+ ve HL or NHL remained in remission, while 5/6 patients with active relapsed disease had a tumor response, which was complete in 4 (Bollard et al., 2007). These studies demonstrated that functional EBV-specific T cells increased in frequency in patient blood after infusion (implying expansion in vivo), homed to tumor tissues and eliminated tumor cells.

Adoptive immunotherapy for virus-independent malignancies. Efforts to exploit adoptively transferred CTLs for treatment of virus-independent cancer has been hindered by (i) limited information regarding expression of TAAs, (ii) lack of reproducible methods to generate CTL lines directed against expressed antigens, given that circulating reactive T cells are often anergized or tolerized, and (iii) immune evasion strategies employed by the tumor which limit the in vivo activity of adoptively-transferred T cells. These include downregulation of expressed target antigens and secretion of inhibitory cytokines that serve to recruit regulatory immune cells to the tumor and directly inhibit and/or re-polarize cytotoxic Th1 T cells to an ineffective Th2 phenotype (Selcean et al., 2009; Formentini et al., 2009; Prokopchuk et al., 2005). The inventors have developed strategies to reactivate anergized/tolerized T cells using optimized antigen presenting cells (APCs) and enhancing cytokines to produce TAA-CTL (Kaka et al., 2009; Foster et al., 2007; Kaka et al., 2008).

The inventors below provide strategies for identifying targets expressed by pancreatic cancer and modulating the response of the in vitro generated TAA-CTLs to the cytokines present in the tumor microenvironment; these strategies are developed to target pancreatic cancer using adoptive immunotherapy.

Determining the pattern of TAA expression There have been limited reports of the TAA expressed by pancreatic cancer biopsy samples. Thus, one can comprehensively document TAA expression in pancreatic cancer using immunohistochemistry (IHC) and RT-PCR, for example.

Generation of TAA-specific CTL in vitro The inventors have developed protocols to generate TAA-CTL from patient PBMC using DCs expressing whole antigen (pepmix or TAA-encoding plasmids) as APCs and co-culture in an optimal cytokine cocktail (Table 1). One can also determine whether this strategy can be applied to the generation of TAA-CTL targeting pancreatic cancer-associated antigens.

Overcoming tumor immune evasion strategies For effective immunotherapy, tumor immune evasion strategies must be characterized and circumvented. Both IL13 and IL4 make a major contribution to inhibiting and repolarizing Th1 effector T cells critical for tumor elimination in pancreatic cancer (Formentini et al., 2009; Prokopchuk et al., 2005). One can characterize arming TAA-CTLs with a chimeric cytokine receptor that binds these inhibitory cytokines and converts their intracellular consequences to a Th1 signal, thus improving the efficacy of the CTLs.

Exemplary Results

Detection of TAA on cancer biopsy samples. To initially model the approach, paraffin embedded 4-µm sections of lymph nodes were obtained from patients with Hodgkin Disease or Follicular B cell lymphoma from the Dept. of Pathology at TCH, The Methodist Hospital, and the Children's Oncology Group. Sections were deparaffinized and rehydrated. Triton-X-100 and Digest ALL1 (Zymed) were used for antigen retrieval. The sections were stained with primary antibodies for MAGE-A4, PRAME, and Survivin. Antigen expression was successfully detected with (i) powervision+kit (immunovision) for rabbit or mouse primary antibodies or (ii) ABC kit (vector labs) for other primary antibodies. All antibodies were validated using positive and negative control slides and a tissue array with non-cancerous tissue.

Generation of TAA-CTL with simultaneous specificity for multiple TAAs using pepmix-pulsed or plasmid-nucleofected APCs. The inventors optimized the CTL generation protocol by using DCs pulsed with a mastermix of pepmixes spanning the exemplary lymphoma-associated antigens SSX2, Survivin, and MAGEA4 as APCs, and co-culturing in the presence of IL7 (10 ng/ml), IL12 (10 ng/ml), IL15 (10 ng/ml) and IL6 (1000 U/ml) (Table 1).

| Group | Th1 polarizing | Proliferation/survival | Inhibits Tregs |
|---|---|---|---|
| 1 | IL-12 | IL7; IL-15 | |
| 2 | IL-12 | IL7; IL-15 | IL-6 |
| 3 | IL-12, IL-27 | IL7; IL-15 | |
| 4 | IL-12, IL-27 | IL7; IL-15 | IL-6 |

TAA-CTL were generated with simultaneous specificity against all three of the stimulating antigens. Importantly, CTL generated from the same donor using the same antigens, but cultured using suboptimal cytokine combinations (Table 1; Groups 1, 3, 4) produced monospecific CTL directed against the immunodominant SSX2 antigen, thus demonstrating the utility of optimizing cytokine combinations to generate multiTM-CTLs, in at least certain embodiments. The consistency and robustness of the system was confirmed by generating multiTM-CTL from 6/6 donors, using DCs nucleofected with DNA plasmids encoding SSX2, Survivin, and MAGEA4. The inventors also generated multiTAA-CTL simultaneously targeting the leukemia-expressed antigens WT1, PRAME, survivin, and Proteinase 3 (n=3) as well as exemplary heptacullular carcinoma-expressed antigens MAGE1, MAGE3 and AFP (n=3). These multiTAA-CTL were functional, as assessed by IFNγ ELispot and cytotoxicity assays. One can apply this technology to the generation of multiTAA-CTL targeting the most frequently expressed pancreatic cancer-expressed antigens.

Figure 2A:
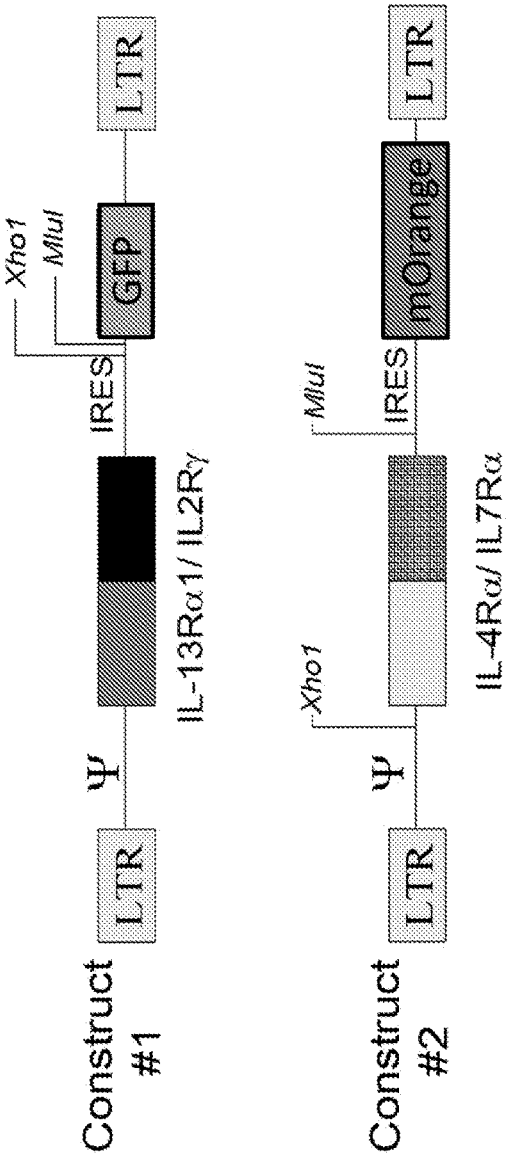
Figure 2B:
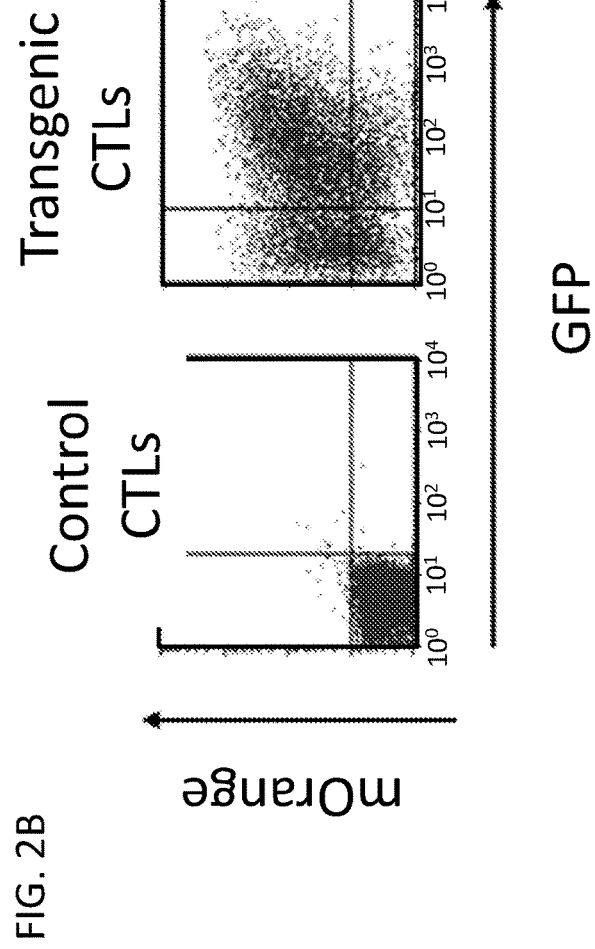

To reverse the effects of Th2 signaling on CTL and ensure exposure to these cytokines instead sustains a Th1 type response engineering 2 intermediate retroviral constructs and preliminary testing in transgenic CTLs. The Th2 cytokines IL4 and IL13, which bind to receptors with shared components, have been reported to suppress Th1 immunity in subjects with pancreatic cancer (Formentini et al., 2009; Prokopchuk et al., 2005). The IL13 receptor is composed of the IL4Rα chain and IL-13Rα1 chain. The IL13 cytokine binds with low affinity to the IL13α1 chain, then recruits the IL4R α chain to increase the binding affinity. In contrast, IL4 first binds the IL4Rα, which then recruits either the IL13Rα1 or the IL2Rγc chain (FIG. 1). Signals from both receptor complexes are transduced by the IL4Rα chain, so that both IL4 and IL13 recruit the same Janus kinase (JAK)-signal transducer and activator of transcription (Stat6) pathway. As a consequence, exposure to either cytokine has overlapping immunoinhibitory consequences (Formentini et al., 2009; Prokopchuk et al., 2005). To counteract these effects on Th1 TAA-CTL the inventors constructed two exemplary first generation retroviral vectors. As presented in FIG. 2A, Construct #1 encodes a fusion protein of the IL13Rα1 exodomain with the IL2Rγ endodomain (IL-13Rα1/IL-2Rγ) linked to GFP through an IRES. Construct #2 encodes a fusion of the IL4Rα exodomain and the IL7Rα endodomain (IL-4Rα/IL-7Rα) linked to mOrange. Thus, cells co-expressing both constructs induce an intracellular Th1 signal upon engagement of either IL4 or IL13 cytokines, in specific embodiments of the invention. To assess the efficiency of retroviral transduction expression of GFP or mOrange was evaluated on double transduced antigen-specific CTLs. As expected this resulted in a mixed population of CTLs that expressed either construct #1 (GFP-positive—lower right quandrant), construct #2 (mOrange-positive—upper left quandrant) or double positive (GFP/mOrange—upper right quandrant) (FIG. 2B). The function of the transgenes was confirmed by measuring phosphorylation of Stat5 after exposure to IL2 (50 U/ml), IL-4(1000 U/ml) or IL13 (5 ng/ml). Phospho Stat5 was detected in control cells only after IL2 administration; in contrast phospho Stat5 was detected in transgenic cells co-expressing both constructs after exposure to any of the 3 cytokines (FIG. 2C). It was confirmed that these cytokines were acting as growth factors using microscopic analyses (FIG. 2D).

Exemplary Experimental Design and Methods

Pancreatic cancer is an aggressive disease with dismal prognosis. Although evidence for tumor-specific T cell immunity exists (Tassi et al., 2008; rong et al., 2009; Plate, 2007; Alters et al., 1997; Cappello et al., 2009; Lepoisto et al., 2008; Kawaoka et al., 2008; Kondo et al., 2008), immunosuppressive cytokines in the tumor environment appear to limit T cell effectiveness (Selcean et al., 2009; Formentini et al., 2009; Kornmann et al., 1999; Prokopchuk et al., 2005). In specific embodiments, infusion of ex vivo expanded TAA-CTL, which have been (i) cultured in Th1 polarizing cytokines to reverse anergy, (ii) selected to be specific for multiple TAAs to minimize escape through epitope loss, and (iii) rendered resistant to inhibitory soluble factors present in vivo produce clinical benefit and offer a novel therapeutic option for pancreatic cancer.

In a first approach, one can do the following: a) assess the cytokine profile of pancreatic tumors, and b) document their pattern of TAA expression. One can establish the pattern of Th1 and Th2/inhibitory cytokines in patients' sera as well as cytokines released from cultured primary tumor samples, determine the pattern of TAA expression in biopsies using IHC and RT-PCR, for example, and generate a bank of DNA plasmids encoding the most frequently expressed antigens for use in CTL stimulation protocols described below. Data from this approach allows design of T cells for adoptive immunotherapy that can be targeted to tumor antigens and made resistant to tumor inhibition.

Exemplary methods are as follows. Cytokine analysis. One can document the cytokine profile of, for example, 30-50 banked patient serum samples and compare these with serum collected from, for example, 30 healthy donors using a Th1/Th2 cytokine array, which detects IL1β, IL2, IL4, IL5, IL6, IL7, IL8, IL10, IL12, IL13, IFNγ, GM-CSF and TNFα; one can measure TGFβ by ELISA. One can also collect fresh biopsy samples, culture for 4-5 days in RPMI+5% HuS and analyze the supernatant using the same cytokines. This allows assessment of the full range of inhibitory and stimulatory cytokines circulating in these patients and being produced by the tumor.

TAA Expression. One can screen biopsy samples for TAA expression, including those previously claimed to be associated with pancreatic cancer (CEA, MUC1, MUC2, MUC5AC, MUC6, and telomerase) (Han et al., 2009; Li et al., 2008) as well as PRAME, MAGEA, SSX2/4, NY-ESO, and Survivin by IHC and RT-PCR.

DNA plasmid bank generation. One can generate plasmids encoding the 7 antigens (by example) most frequently detected in screening. These can be cloned into a p-Max expression plasmid under the control of a CMV promoter, which ensures high levels of transgene expression and will be co-expressed with GFP to enable assessment of nucleofection efficiency. The inventors have previously validated DNA plasmids as an effective source of antigen for the generation of both virus (Gerdemann et al., 2009) and tumor-specific CTL.

In specific embodiments of the invention, one detects a predominance of the Th2/inhibitory cytokines IL13 and IL4 in patient sera and in supernatant from cultured biopsies, because both are produced in excess by pancreatic cell lines and used by the tumor as autocrine growth factors. In specific embodiments one detects TAA expression on patient biopsies. Published reports indicate that the majority of tumors are CEA-positive, approximately 60% express MUC-1, while MUC-6 is less frequently detected (<15%), and one can further characterize frequency and intensity of TAA expression. A plasmid bank expressing the most frequently detected TAAs may be generated.

TABLE 2

Exemplary Tissue Samples

| Tissues | Number of Samples |
|---|---|
| Blood cells | 232 |
| Cyst fluid | 22 |
| Normal Tissue | 701 |
| Pancreas juice | 66 |
| Plasma | 574 |
| Serum | 559 |
| Tumor Tissue | 780 |
| Pancreatitis | 178 |
| Total | 3092 |

These described embodiments provide the profile of TAA and inhibitory cytokine expression by pancreatic tumors, allowing design of targeting and protective strategies.

In a second approach, one can generate tumor-specific CTL specific for multiple pancreatic cancer-associated target antigens and evaluate their specificity and function in vitro. One can determine whether CTL directed against pancreatic cancer TAAs can be expanded from subjects with pancreatic cancer. One can generate CTL, first with single and then with multi-antigen specificity, based on success in other cancers, with the intent of minimizing immune evasion mediated by tumor antigen loss variants.

Exemplary methods are as follows: One can obtain, for example, 40-50 ml of patient blood that will be a source of APCs and responder T cells. One can generate CTL lines from 20-25 patients, for example.

DC generation: DCs are differentiated from CD14-selected monocytes by culture in GM-CSF and IL-4 in CellGenix DC medium. CD14-positive cells are cryopreserved for subsequent stimulation. The cultured DCs re matured for 24 hrs, nucleofected using the different antigen-encoding DNA plasmids generated as described above, for example, then matured for a further 24 hrs. Phenotype and nucleofection efficiency are assessed by measuring expression of maturation/co-stimulatory molecules CD80, CD83, CD86, HLA-Dr and GFP using flow cytometry.

CTL stimulation: For activation of antigen-specific T cells, nucleofected DCs are co-cultured with the CD14-positive PBMCs at a R:S ratio of 10:1 in CTL medium (45% Click's, 45% advanced RPMI, 5% human serum and 5 mM L-glutamax) in the optimized cytokine cocktail (IL-7, IL-12, IL15 and IL6) (Table 1) to promote optimal CTL survival and expansion. To generate multiTAA-CTL one can transfect DCs with multiple plasmids simultaneously. The expanded cells are restimulated on day 9 with nucleofected DCs and cultured with IL7, and twice weekly IL-2 (50 U/ml) from day 12. CTL expansion and viability are assessed by trypan blue exclusion. After 3 stimulations, one can analyze cell phenotype using markers including CD4, CD8, CD56, CD16, CD45RA, CD45RO, CD25, CD28, CD27, and CD62L to determine the activation and memory (effector vs. central memory) status of the CTL. One can measure production of Th1 (IFN-γ, TNFα, IL2) and Th2 (IL4, IL5, IL13, IL10, and TGFβ) cytokines in response to stimulation (either peptides or nucleofected DCs), using ELispot or intracellular cytokine staining. Epitope breadth is assessed by ELispot, for example, using overlapping peptide pools to stimulate CD4 and CD8 selected cells and it is determined which CD4 and CD8 epitopes are recognized within each protein. Cytolytic function is assessed by $Cr^{51}$ release assay using TAA-expressing APCs, HLA-matched pancreatic cell lines, as well as autologous tumor as target cells.

In specific embodiments of the invention, polyclonal multiTAA-CTL re readily produced from patient PBMC using nucleofected DCs as APCs. In certain cases not all the antigens are immunogenic in all donors, although in specific cases one can consistently generate multiTAA-CTL recognizing at least 2 antigens for each subject. Based on findings in CTL lines in combination with the TAA expression profile identified as described above, one can identify the optimal 4-5 targets (for example) for future immunotherapy. The expanded cells may be polyclonal (CD4+ and CD8+) with populations of central (CD62L+) and effector memory (CD62L−), and terminally differentiated effectors. In the presence of the optimized cytokine cocktail, in specific embodiments the CTL will have a Th1 cytokine profile and will produce TNFα, IFNγ, and IL2 upon restimulation, allowing identification of a panel of CD4+ and CD8+ T cell epitopes for each antigen. In some embodiments of the invention, the expanded cells retain specificity and activity for all the stimulating antigens as measured by flow cytometry, intracellular cytokine staining, and cytolytic assays, for example.

In cases where there may be failure to generate TAA-CTL using nucleofected DCs as APCs, one can utilize pepmixes for antigenic stimulation. In cases where there may be failure to simultaneously activate and expand CTL with multiTAA specificity, as for viral antigens, not all TAAs are equally immunogenic and one may see antigenic competition and loss of specificity against weaker antigens over multiple rounds of stimulation. However, the optimized cytokine combination enables one to sustain multispecificity within the lines. In cases wherein there may be poor proliferation of TAA-CTL in vitro (although this is unlikely because the inventors consistently achieve 20-40 fold expansion of TAA-CTL over a 16 day culture period in a G-Rex bioreactor; Vera et al., 2009), but if this expansion is not sustained one can substitute IL15 for IL2 that augments proliferation without loss of specificity (Quintarelli et al., 2007). In cases wherein the frequency of reactive T cells is below the limit of detection of the IFNγ ELispot and intracellular staining assays, although this is unlikely because the ELIspot can detect as few as 1/100,000 cytokine-secreting cells, one can analyze CTL that have been multiply stimulated (and doubled 7-10 times each stimulation, for example) so one would expect that the frequency of T cells is sufficiently amplified to allow detection. If not, one can restimulate.

In embodiments of the invention, there is developed a reproducible technique to manufacture polyclonal CTL with specificity for multiple epitopes within multiple tumor antigens expressed in cancer, including at least pancreatic cancer.

In a third approach, one can protect CTLs from the inhibitory effects of signaling with Th2 cytokines by forced expression of chimeric cytokine receptors. In particular embodiments, there is generation of a single bicistronic construct encoding the exodomains of the IL13Ra and/or IL4Ra linked to the endodomains of IL2Rγ and/or IL7Rα, for example.

One tumor immune evasion strategy employed by pancreatic cancer, for example, is the release of Th2-inhibitory cytokines, such as IL13 and IL4, which i) enhance cancer cell proliferation and ii) attenuate and re-polarize TAA-specific Th1-CT1 to Th2 cells. Thus to improve the efficacy of adoptively-transferred multiTAA-CTL one can render them resistant to the inhibitory effects of IL13 and IL4 using a chimeric cytokine receptor that links the exodomains of the receptors that bind these Th2 cytokines to the signaling endodomains of two stimulatory (Th1) cytokine receptors.

Figure 3:
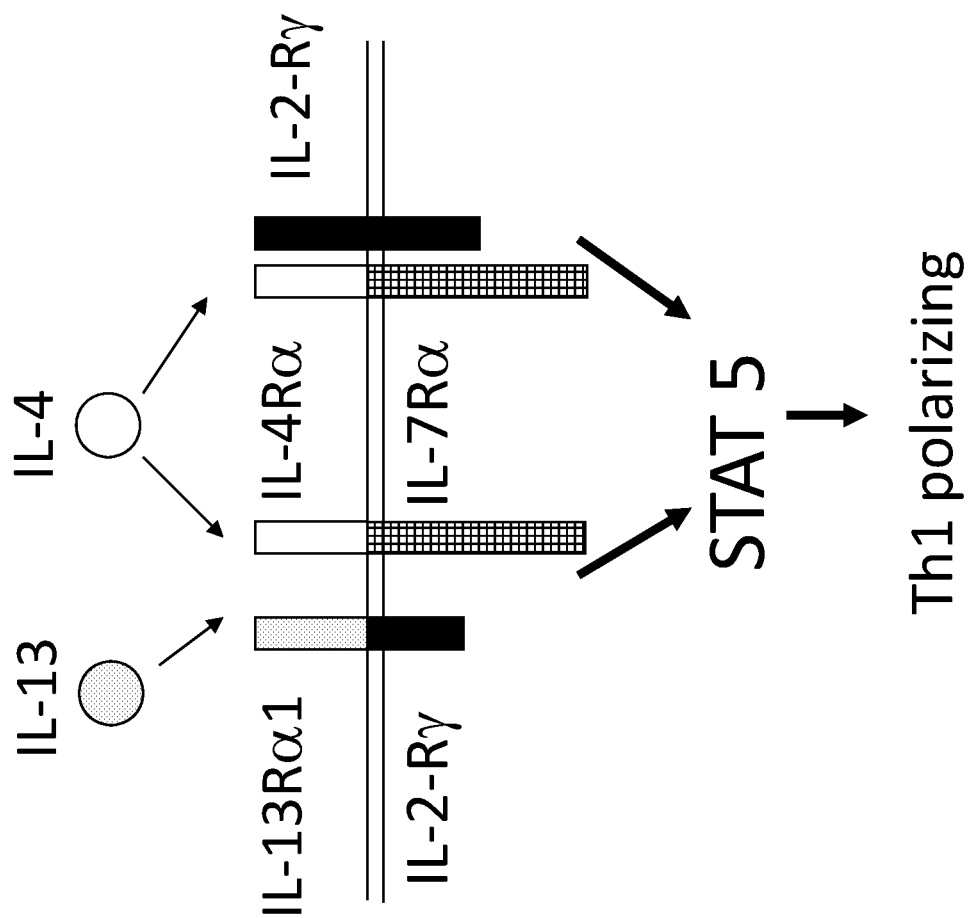
FIG. 3. Exemplary Construct #3 a Schematic of IL4 and IL13 signaling in transgenic cells.

Exemplary methods are as follows: The inventors have already prepared and tested 2 exemplary functional intermediate retroviral vectors; construct #1 encodes IL-13Rα1/IL-2Rγ-IRES-GFP and construct #2 encodes IL-4Rα/IL-7Rα-IRES-mOrange (FIG. 2). Unique compatible restriction enzyme sites (Xhol-Mlul) were included to allow easy replacement of GFP in construct #1 with the IL4Rα/IL7Rα fusion protein from construct #2 (FIG. 2a) in order to produce a single bicistronic construct (#3) that encodes the exodomains for both IL4 and IL13 receptors with the signal transducing IL2 and IL7 receptors (FIG. 3). One can validate its function by standard means in the art. Retroviral supernatant can be prepared using transient transfection of 293T cells and CT1 transduction can follow published protocols (Vera et al., 2009; Quintarelli et al., 2007; Vera et al., 2006; Savoldo et al., 2007). One can evaluate the expression of recombinant proteins by FACS analysis for IL13Rα and IL4Rα, and the functionality of the IL2Rγ and IL7Rα endodomains by phospho Stat 5 analysis in the presence of IL2, IL4 or IL13. One can then generate a stable PG-13 producer line containing the Gag and Pol sequences in trans, allowing stable virus production. One can isolate single cell clones and test them for functional titers and replication competent vector.

In specific embodiments of the invention, there is equal expression of both IL13Rα1 and IL4Rα as evaluated by FACS, and that both IL2Rγ and IL7Rα endodomains will transmit a Th1 signal detectable by phospho Stat5 analysis. There is transducing of >20% of T cell targets, for example, and transduced cells are selected over time by culture in IL4 or IL13 (Vera et al., 2009; Bollard et al., 2007; Savoldo et al., 2007).

In some cases there may be cross-pairing between the IL13Rα1 exodomain and the wildtype IL4Rα, which is weakly expressed on CTL, and this could result in low level background Stat6 signaling. However, the high ratio of transgenic:wildtype receptor expression decreases the probability that this will occur. Cross-pairing of the IL4Rα exodomain with the wild type IL2Rγ may also occur in certain aspects, but in this is acceptable because a Th1 signal will be transmitted (FIG. 3).

In some embodiments of the invention, there is produced a bicistronic construct and stable producer line that enables CTL to sustain Th1 activity signal even when exposed to IL4 or IL13 that normally induce a Th2 switch.

One can assess the ex vivo transduction efficiency and function of gene-modified multiTAA-CTL cultured in the presence of IL13 and IL4. This formal in vitro comparison allows determination whether each fusion protein is expressed functionally in multiTAA-CTLs, whether transgene expression persists, and whether such expression alters the phenotype of the transduced cells, or adversely affects their anti-tumor activity.

Exemplary methods are as follows: multiTAA-CTLs are generated as described above, for example, and transduced with construct #3, for example. One can measure expansion of non-transduced and transduced cells. CTL that have been singly transduced with either construct #1 or #2 may be used as controls. CTLs are cultured in the presence of IL2, IL4 and IL13. One can measure changes in cell phenotype, numbers and viability using FACs and trypan blue exclusion, and changes in cell signaling using a Multi-pathway signaling kit. In addition, the anti-tumor activity is compared using autologous TAA-expressing APCs, HLA-matched pancreatic cell lines, and autologous tumor cells as targets in the presence of IL2, IL13 and IL4 in a short (4 hr $Cr^{51}$, assay) and long-term (4 day co-culture) study.

In specific aspects of the invention, one detects functional levels of both fusion proteins and that culture of nontransduced CTLs or CTLs transduced with construct #1 with any cytokine other than IL2 produces a negative effect on CTL function, proliferation and survival. In a specific embodiment, CTLs transduced with construct #2 proliferate and maintain their function in the presence of IL4, because this exemplary chimeric construct can dimerize with wildtype IL2Rγ. Finally, CTL transduced with construct #3 transmit a Th1 signal, proliferate, survive and function in the presence of all three cytokines (FIG. 3), in specific embodiments of the invention. A summary table of exemplary results is shown in Table 3.

TABLE 3

Predicted Results for Exemplary Constructs

|  | +IL2 Growth/Function | +IL4 Growth/Function | +IL13 Growth/Function |
|---|---|---|---|
| Non-transduced | +++ | − | − |
| #1 (IL13Rα/IL2Rγ) | +++ | − | − |
| #2 (IL4Rα/IL7Rα) | +++ | ++ | − |
| #3 (fusion) | +++ | ++++ | ++++ |

In embodiments of the invention, tumor-targeted multi-specific CTL therapy is developed for cancer, such as pancreatic cancer, and these cells are made resistant to an important immune evasion strategy used by the tumor. One can produce and infuse gene-modified multiTAA-CTL in a clinical study to evaluate their safety and anti-tumor efficacy in individuals with pancreatic cancer.

Example 2

Genetic Modification of Car-Modified T Cells with IL4Rα/IL7Rα as Example

Tumors have evolved complex mechanisms to subvert the cellular immune response including expression of FasL or PD-L1 that induce anergy or apoptosis in effector T cells. Included in the microenvironment are recruitment of regulatory T cells and secretion of TGF-β and other immunosuppressive cytokines that inhibit T cell proliferation. There is constitutive expression of indoleamine 2,3-dioxygenase (IDO) by tumors and regulatory dendritic cells, which depletes tryptophan, resulting in T cell anergy and down-regulation or modulation of MHC and co-stimulatory molecules. T cells can be suppress by a diverse of factor present in the tumor microenvironment, including at least IL10, TGF-β, IL13, and IL-4. One can overcome this problem if a cytokine receptor exo-domain is used with a normative endodomain to arm the T cells to withstand the inhibitory tumor microenvironment.

Figure 4:
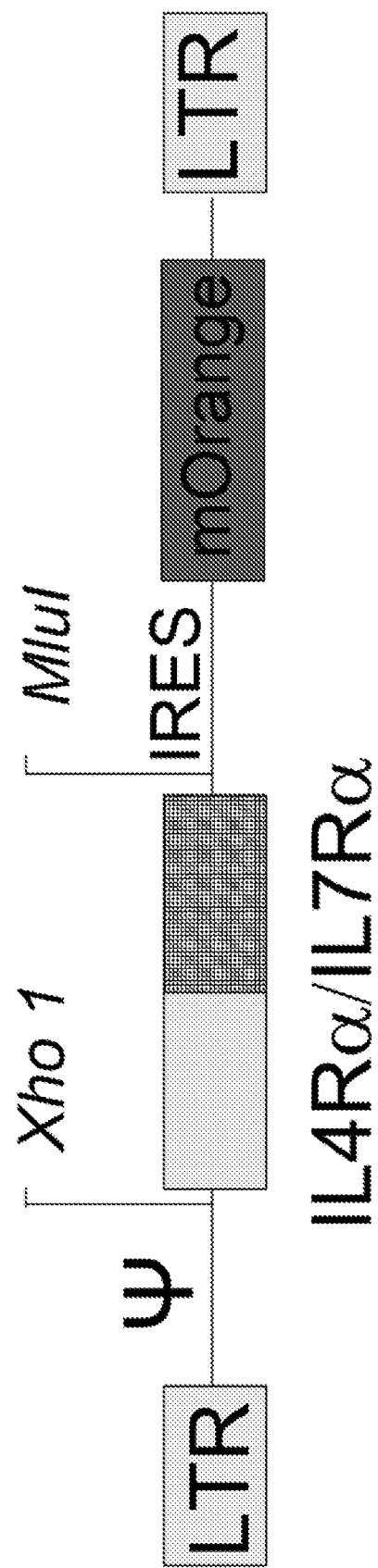
FIG. 4 Exemplary fusion of IL4Rα/IL7Rα ("4/7R") and a reporter gene
Figure 5:
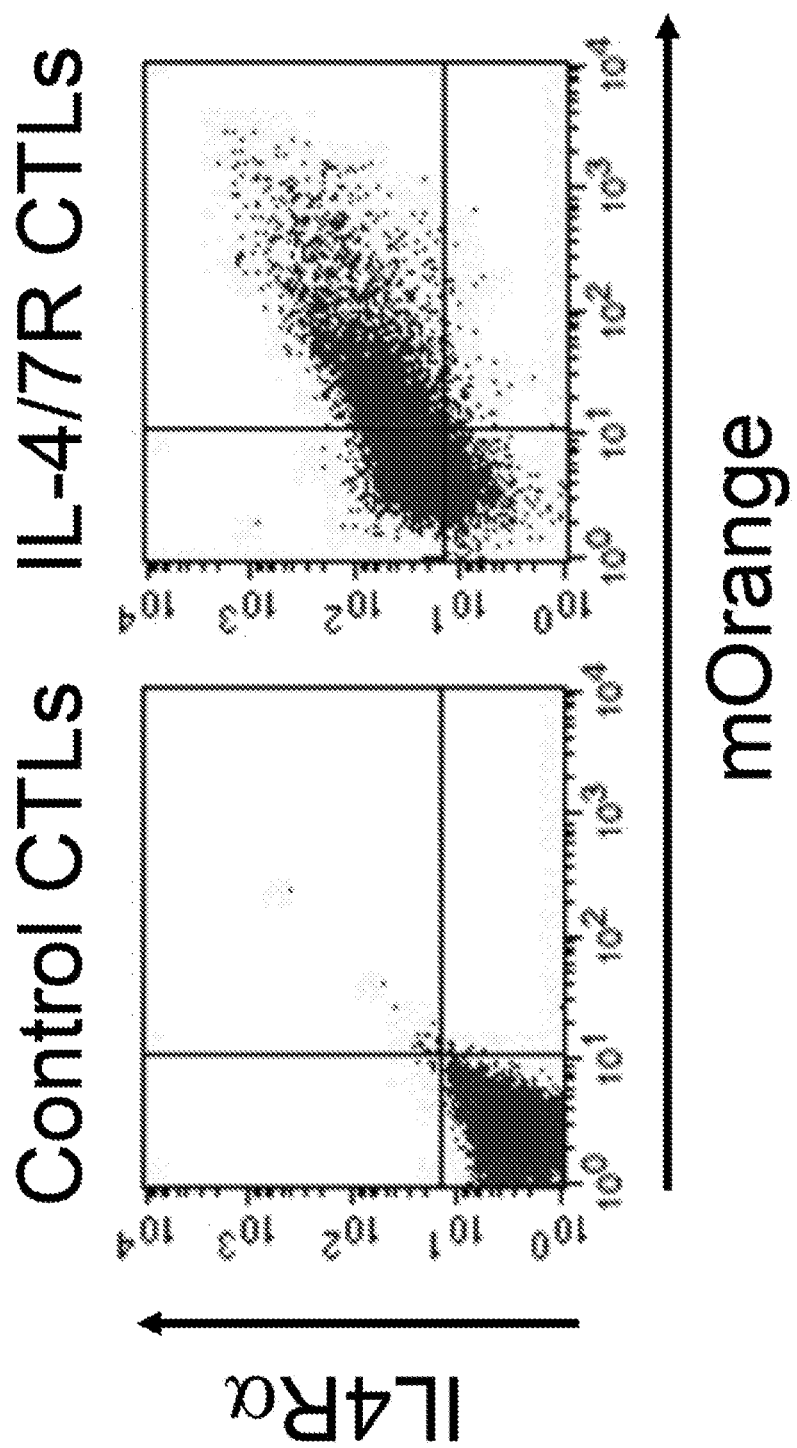
FIG. 5 shows stable expression of IL4R and mOrange on transduced cells.
Figure 6:
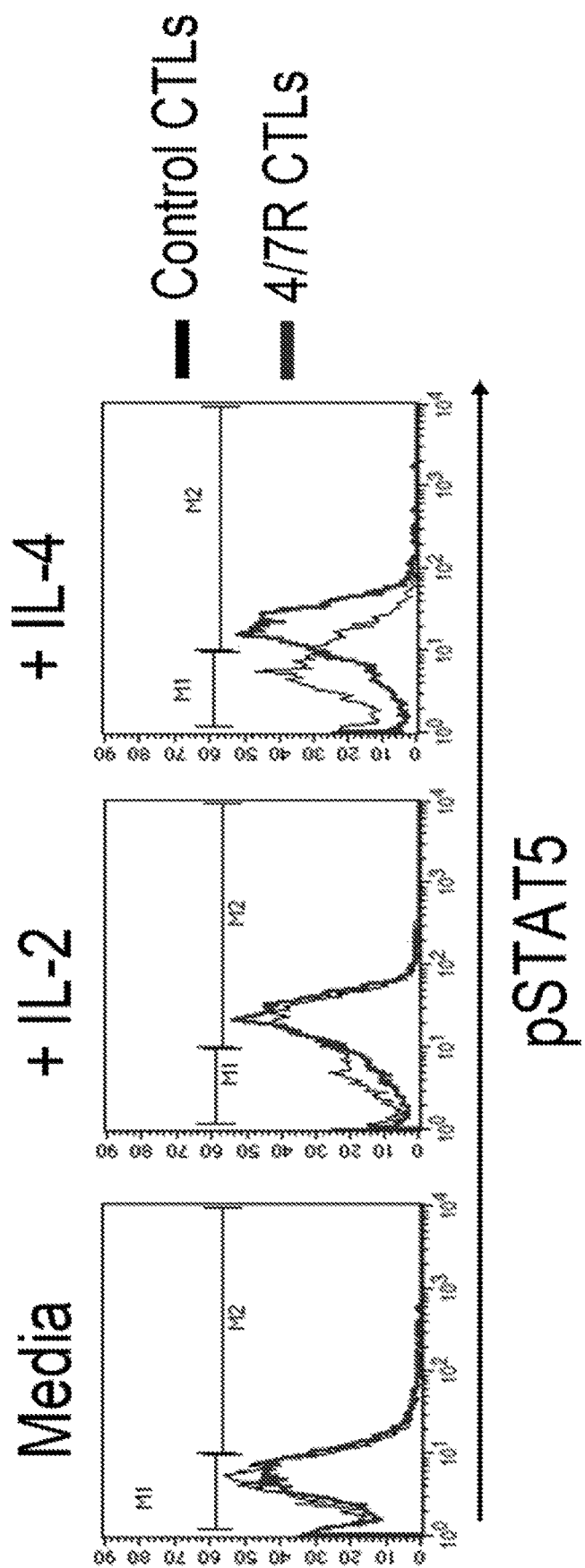
FIG. 6 shows pSTATS on transgenic cells after IL-4 administration.
Figure 7:
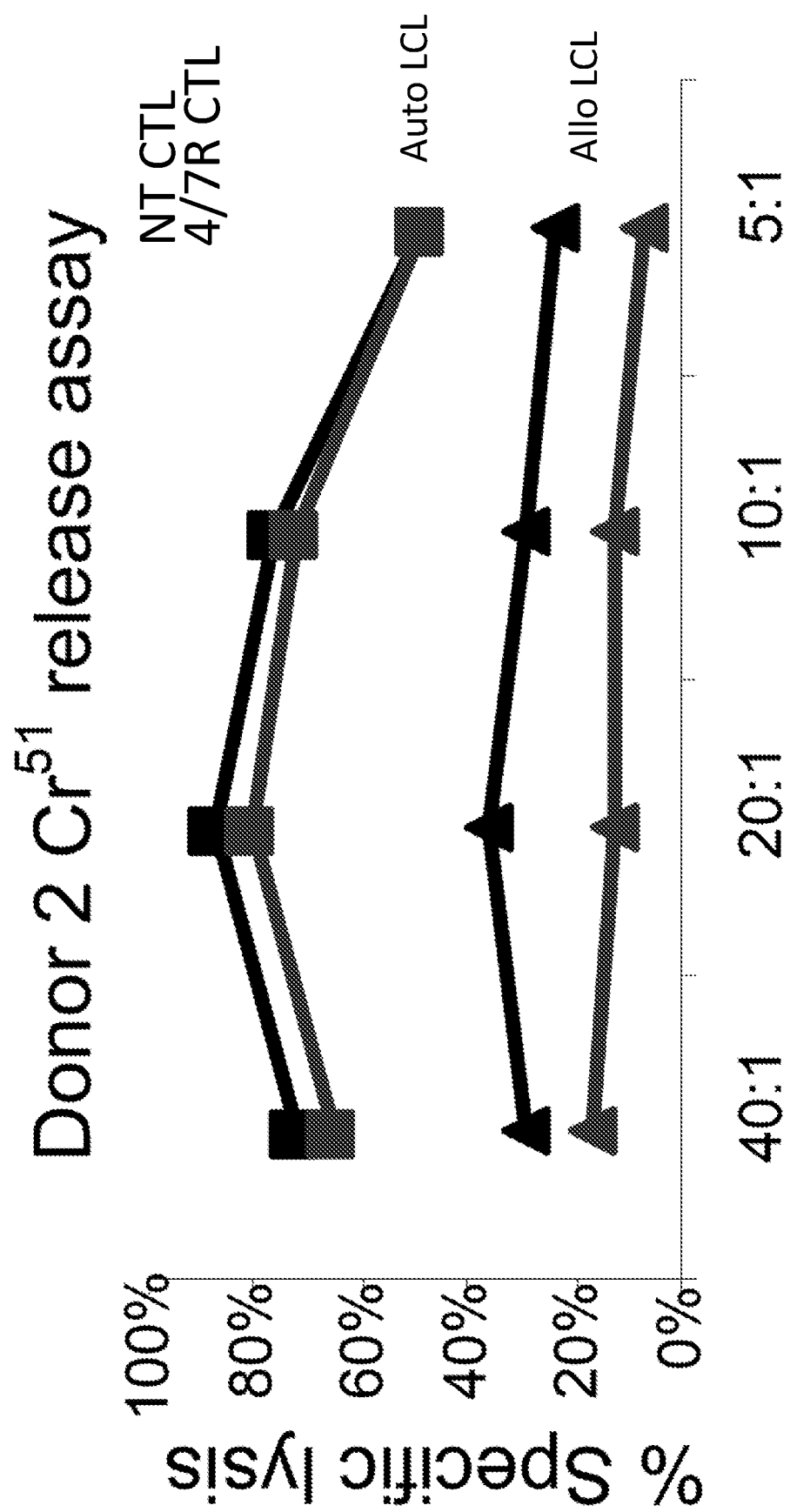
FIG. 7 demonstrates that 4/7R expression does not adversely affect CTL function.
Figure 8:
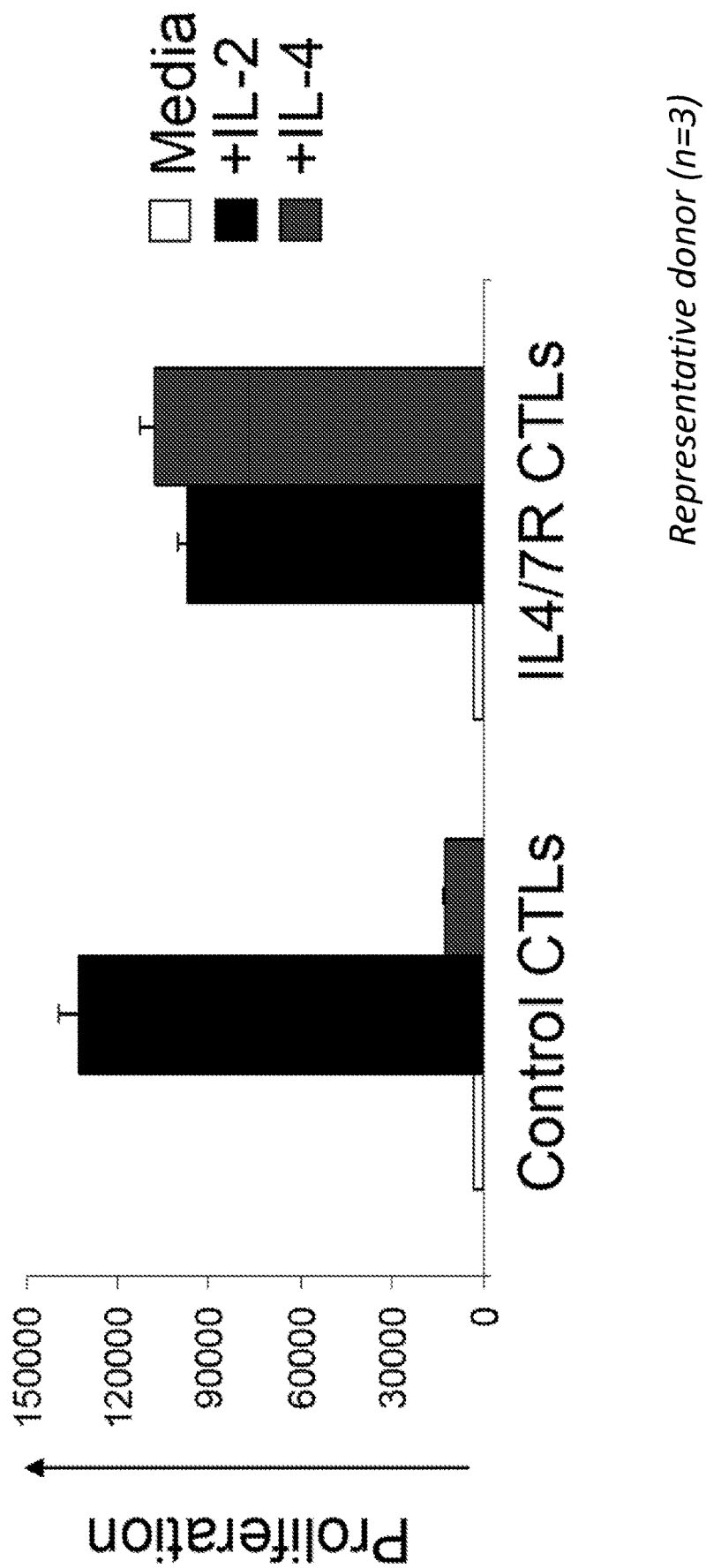
FIG. 8 shows that transgenic T cells expressing 4/7R proliferate in vitro in the presence of IL-4.
Figure 9:
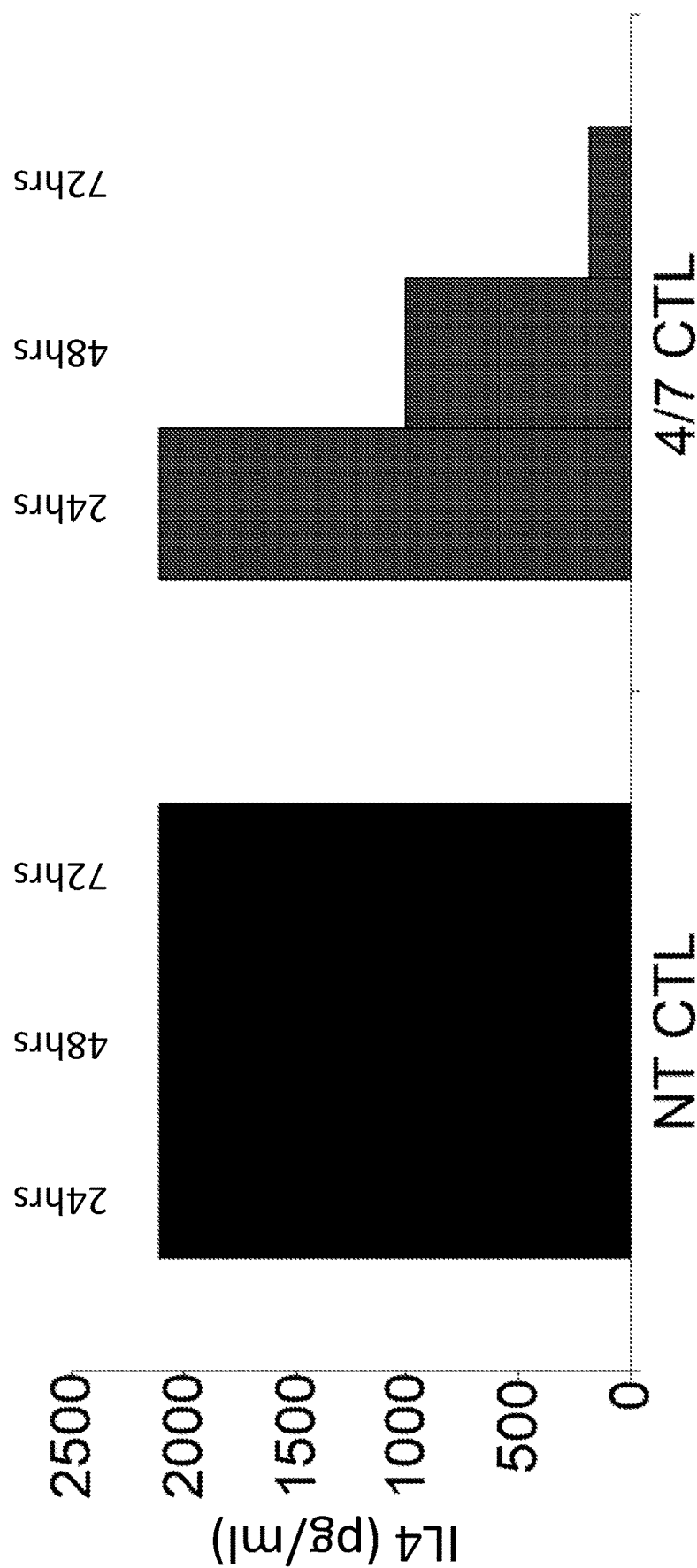
FIG. 9 shows that 4/7R-expressing CTL can deplete IL4 from supernatant.
Figure 10:
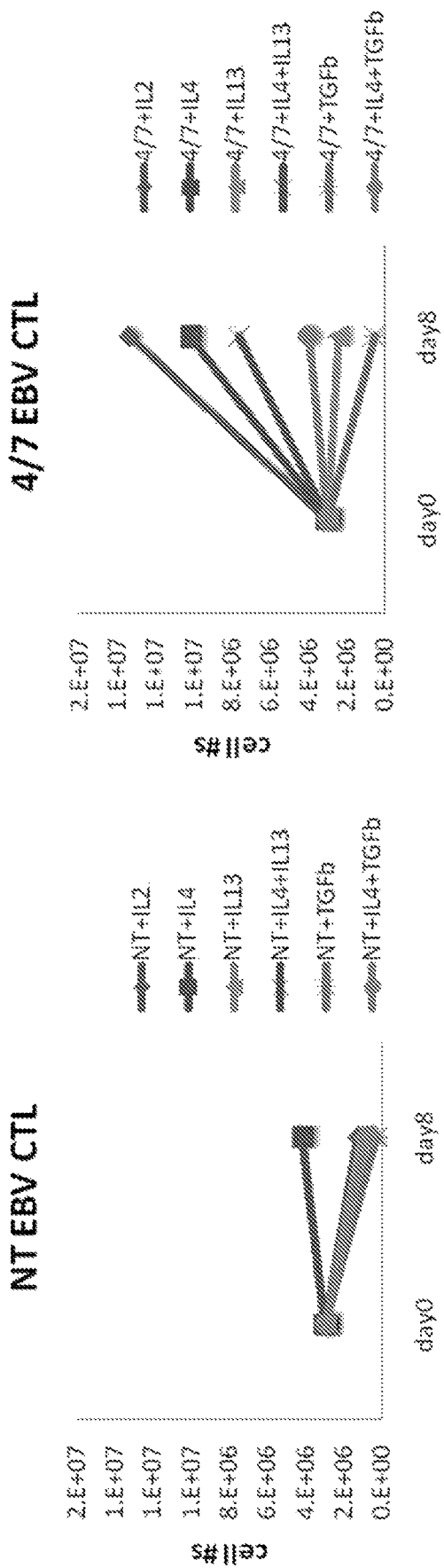
FIG. 10 demonstrates that 4/7R-expressing CTL are resistant to other immuno suppressive cytokines.

In embodiments of the invention there is protection of multiTAA-CTLs from the inhibitory effects of Th2 cytokines by forced expression of an artificial IL4/1L7 cytokine receptor. An exemplary transgenic construct may be produced, such as one in FIG. 4, that illustrates a fusion of IL4Rα/IL7Rα and includes a reporter gene, such as mOrange, although in some cases the construct lacks a reporter gene. FIG. 5 demonstrates stable expression of the transgenic receptor as detected by flow cytometry to detect expression of the IL4R and co-expression of mOrange on transduced cells. FIG. 6 shows that the transgenic receptor is functional as assessed by the detection of phosphorylated STAT5 (pSTAT5) in transgenic cells upon exposure to the IL4 cytokine, which under wildtype conditions would induce pSTAT6. FIG. 7 demonstrates that transgenic expression of the chimeric 4/7R does not adversely affect CTL function, as assessed using a chromium release assay to detect specific lysis of target cells, and FIG. 8 shows that transgenic T cells expressing 4/7R proliferate in vitro in the presence of either IL2 (standard growth factor used to induce T cell proliferation) or IL-4 while CTLs generated from the same donors but not expressing the 4/7R are able to proliferate only in the presence of the growth factor IL2. FIG. 9 shows that 4/7R-expressing CTL can deplete IL4 from supernatant collected from a tumor line, indicating that indeed the transgenic receptor can utilize tumor-produced cytokine and may potentially starve the tumor of an erstwhile growth factor. FIG. 10 shows that 4/7R-expressing CTL are resistant to other immunosuppressive cytokines as assessed by cell counted after exposure to the indicated cytokine conditions; CTL specificity and function were maintained as assessed by ELIspot.

Figure 11:
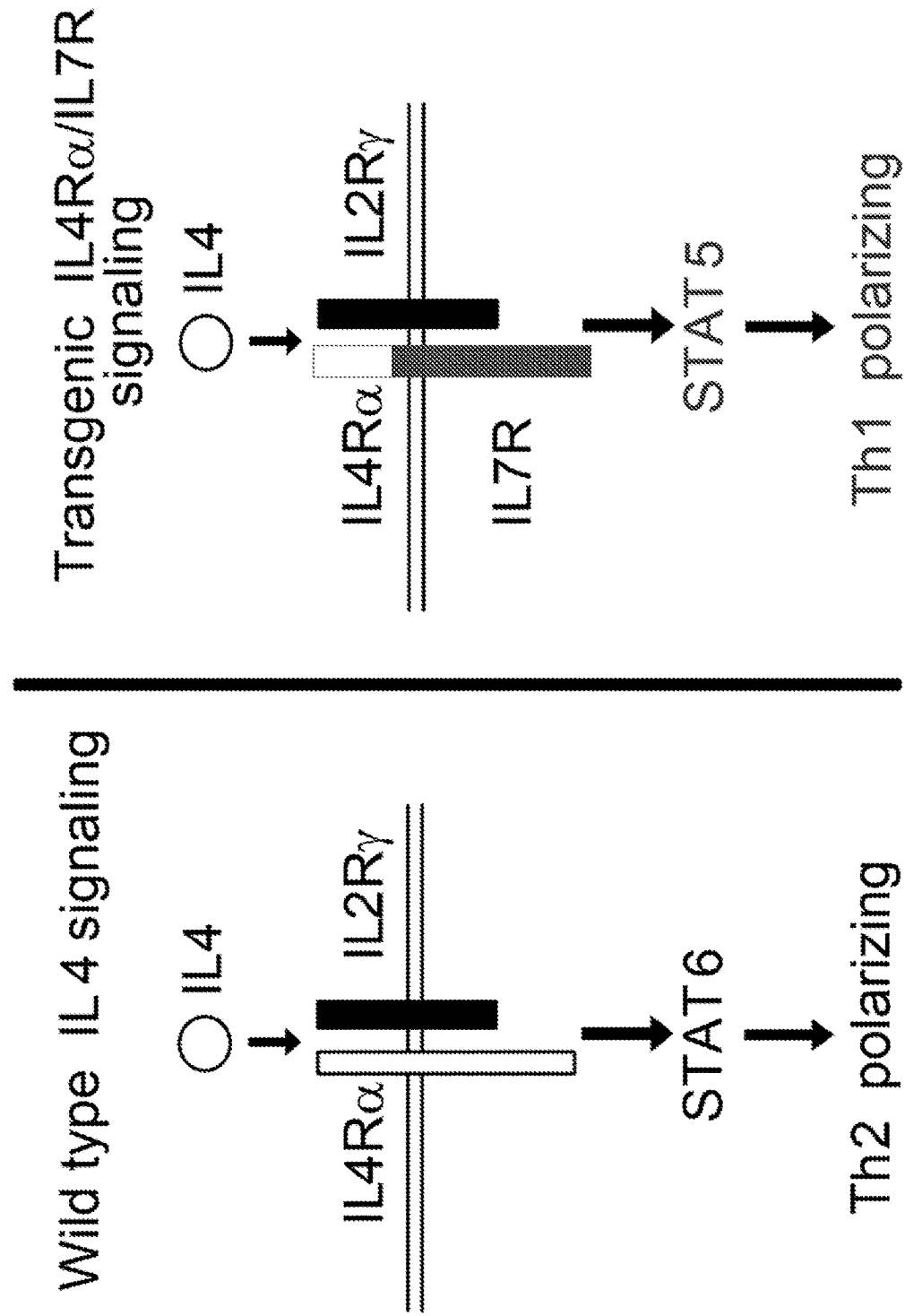
FIG. 11 illustrates changing the signaling of an immunosuppressive cytokine into a T cell growth factor.
Figure 12:
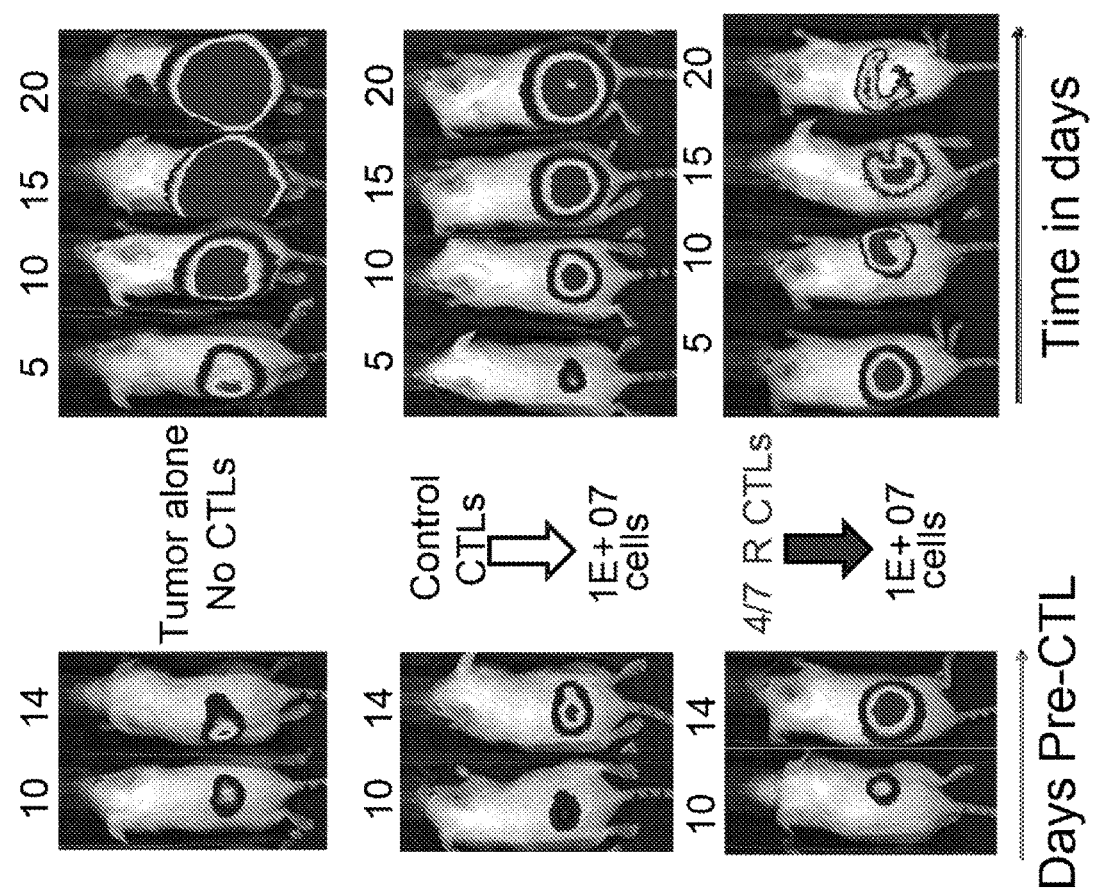
FIGS. 12-14 demonstrate that 4/7R CTLs control tumor growth.
Figure 13:
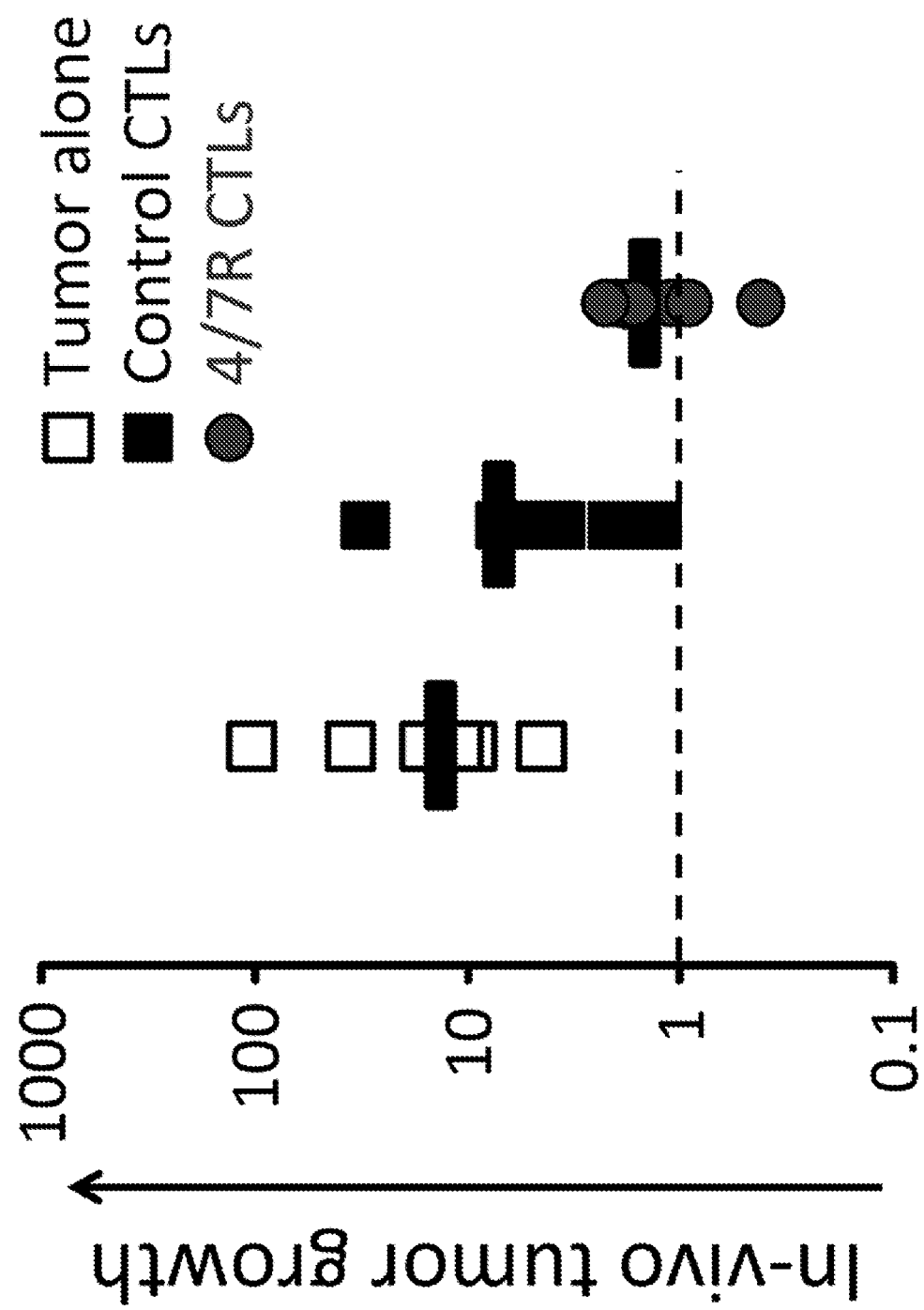
Figure 14:
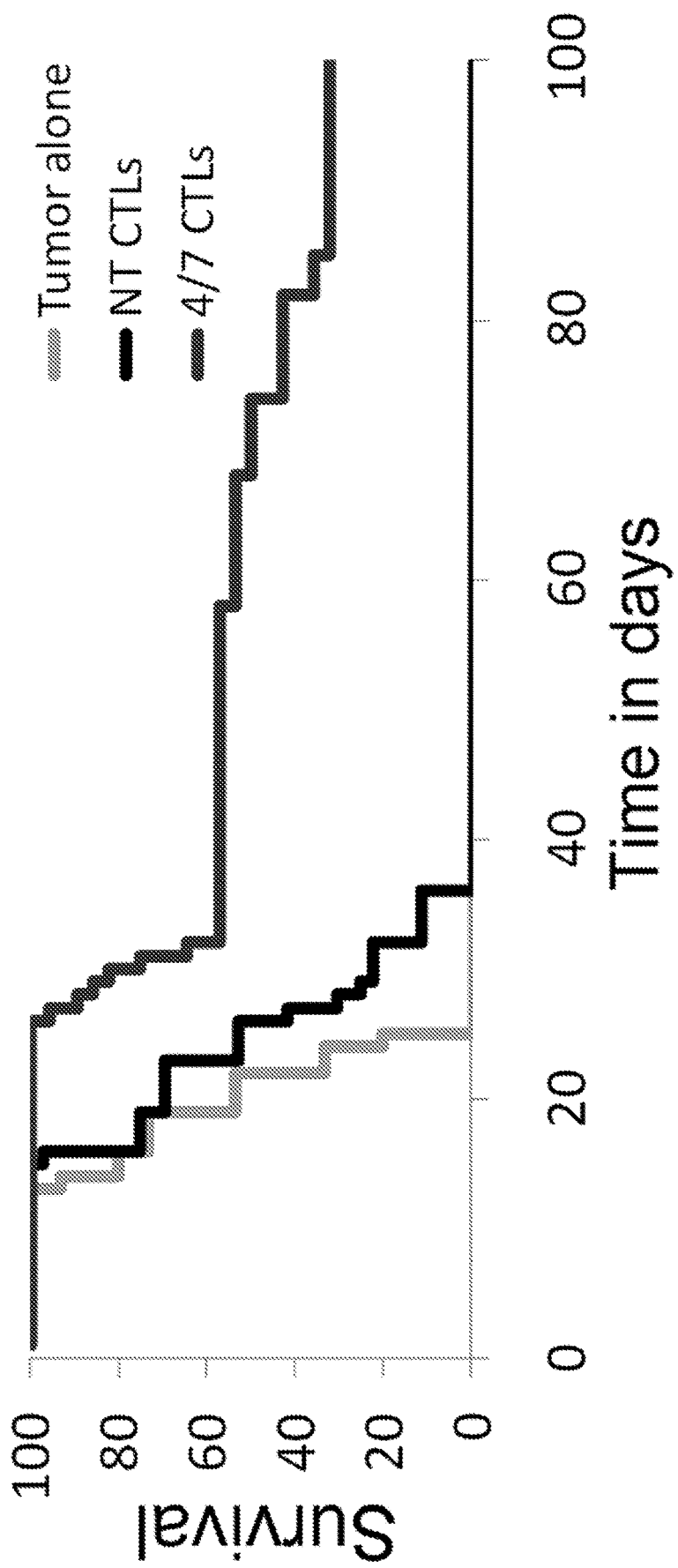
Figure 15:
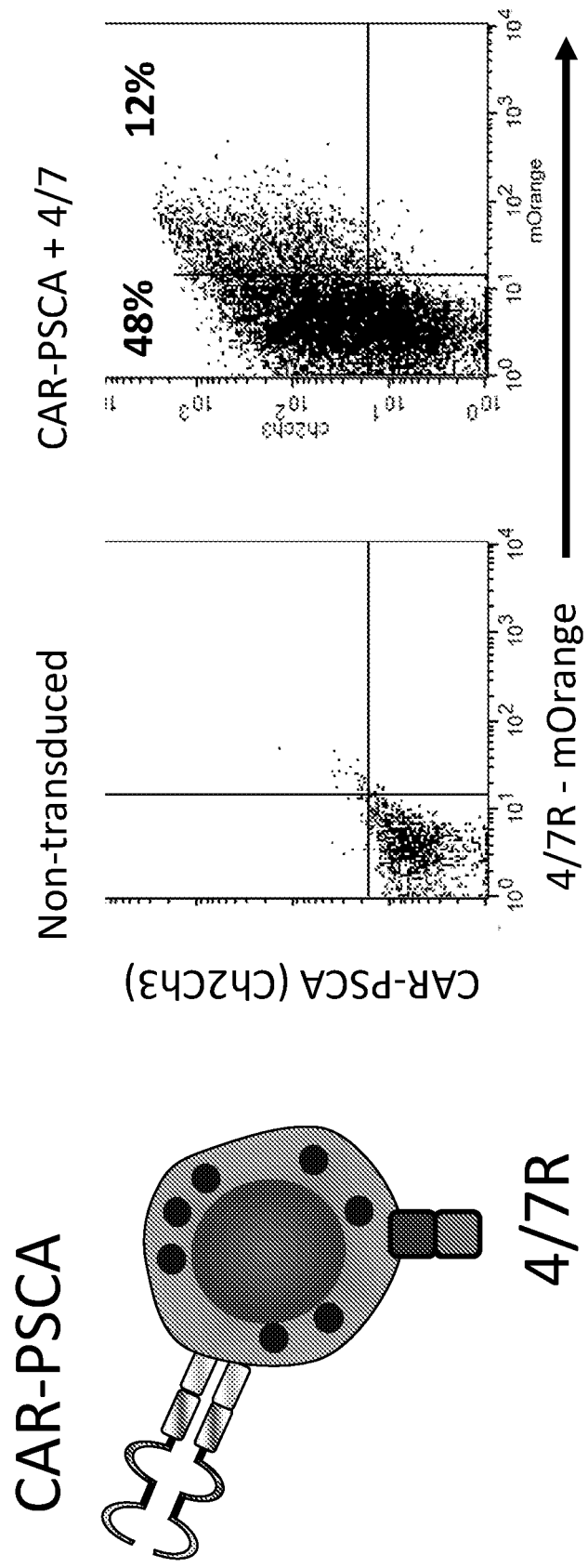
FIG. 15 addresses that in certain embodiments one can modify patient-derived CAR-PSCA modified T cells to co-express 4/7R, for example.
Figure 16:
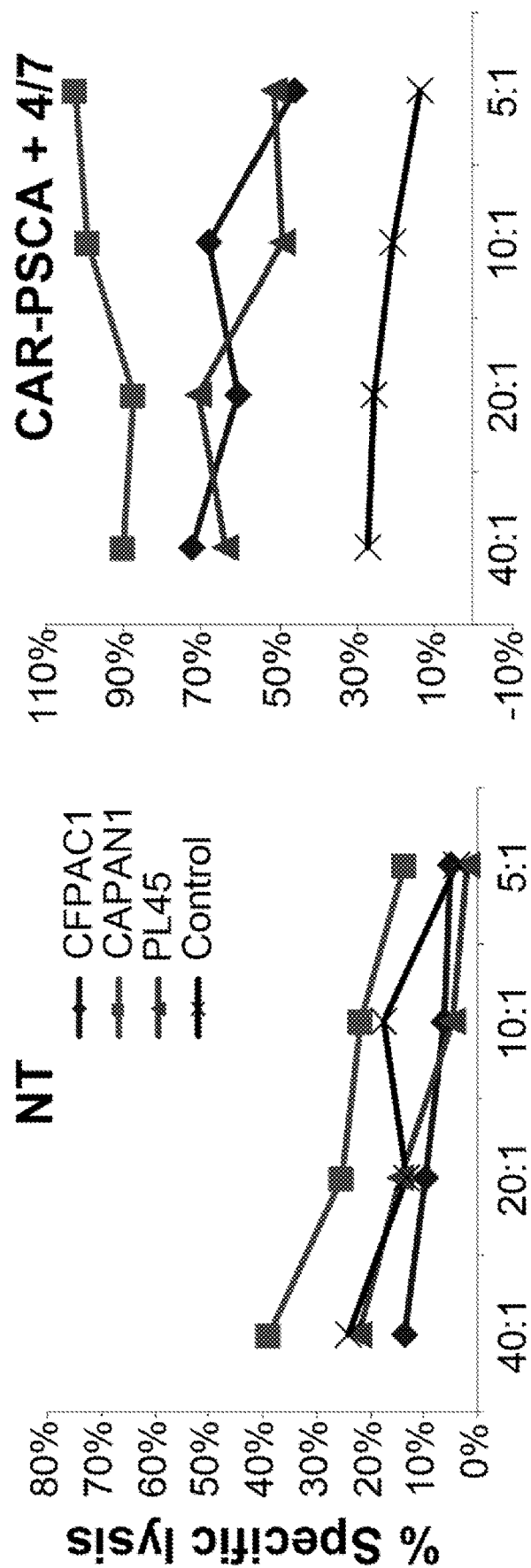
FIG. 16 shows that CAR-PSCA T cells modified to co-express 4/7R retain their ability to kill tumor targets.

Changing the signaling of an immunosuppressive cytokine into a T cell growth factor is illustrated (FIG. 11). FIG. 12-14 demonstrate that 4/7R CTLs control tumor growth in a xenograft mouse model where SCID mice were engrafted with an IL4-producing tumor co-expressing FFLuc to allow in vivo imaging. Subsequently animals were treated with non-transduced or 4/7R-modified CTLs. Animals treated with 4/7R CTLs had significantly smaller tumors that control groups which resulted in an increase in overall survival. FIG. 15 addresses that in certain embodiments one can modify patient-derived CAR-PSCA modified T cells to co-express 4/7R, for example. FIG. 16 shows that CAR-PSCA T cells modified to co-express 4/7R retain their ability to kill tumor targets.

This example shows that T cells can be modified to co-express different transgenes. T cells were conferred with antigen specificity via genetic modification with a chimeric antigen receptor targeting the exemplary tumor antigen PSCA. Subsequently the same cells were modified to co-express the 4/7R. Modification with 4/7R did not adversely affect to ability of the T cells to recognize tumor cells.

REFERENCES

Alters S E, Gadea J R, Philip R. Immunotherapy of cancer. Generation of CEA specific CTL using CEA peptide pulsed dendritic cells. Adv. Exp. Med. Biol. 1997; 417:519-524.

Bollard C M, Aguilar L, Straathof K C et al. Cytotoxic T lymphocyte therapy for Epstein-Ban virus+Hodgkin's disease. J. Exp. Med. 2004; 200:1623-1633.

Bollard C M, Gottschalk S, Leen A M et al. Complete responses of relapsed lymphoma following genetic modification of tumor-antigen presenting cells and T-lymphocyte transfer. Blood 2007; 110:2838-2845.

Cappello P, Tomaino B, Chiarle R et al. An integrated humoral and cellular response is elicited in pancreatic cancer by alpha-enolase, a novel pancreatic ductal adenocarcinoma-associated antigen. Int J Cancer 2009; 125:639-648.

Formentini A, Prokopchuk O, Strater J et al. Interleukin-13 exerts autocrine growth-promoting effects on human pancreatic cancer, and its expression correlates with a propensity for lymph node metastases. Int. J. Colorectal Dis. 2009; 24:57-67.

Foster A E, Leen A M, Lee T et al. Autologous designer antigen-presenting cells by gene modification of T lymphocyte blasts with IL-7 and IL-12. J Immunother 2007; 30:506-516.

Gerdemann U, Christin A S, Vera J F et al. Nucleofection of DCs to generate Multivirus-specific T cells for prevention or treatment of viral infections in the immunocompromised host. Mol. Ther. 2009; 17:1616-1625.

Han L, Pansare V, AI-Abbadi M, Husain M, Feng J. Combination of MUC5ac and WT-1 immunohistochemistry is useful in distinguishing pancreatic ductal carcinoma from ovarian serous carcinoma in effusion cytology. Diagn. Cytopathol. 2009

Heslop H E, Ng C Y C, Li C et al. Long-term restoration of immunity against Epstein-Barr virus infection by adoptive transfer of gene-modified virus-specific T lymphocytes. Nature Medicine 1996; 2:551-555.

Heslop H E, Siobod K S, Pule M A et al. Long term outcome of EBV specific T-cell infusions to prevent or treat EBV-related lymphoproliferative disease in transplant recipients. Blood 2009

Kaka A S, Foster A E, Weiss H L, Rooney C M, Leen A M. Using dendritic cell maturation and IL-12 producing capacity as markers of function: a cautionary tale. J Immunother 2008; 31:359-369.

Kaka A S, Shaffer D R, Hartmeier R et al. Genetic modification of T cells with IL-21 enhances antigen presentation and generation of central memory tumor-specific cytotoxic T-lymphocytes. J Immunother 2009; 32:726-736.

Kawaoka T, Oka M, Takashima M et al. Adoptive immunotherapy for pancreatic cancer: cytotoxic T lymphocytes stimulated by the MUC1-expressing human pancreatic cancer cell line YPK-1. Oncol. Rep. 2008; 20: 155-163.

Kondo H, Hazama S, Kawaoka T et al. Adoptive immunotherapy for pancreatic cancer using MUC1 peptide-pulsed dendritic cells and activated T lymphocytes. Anticancer Res. 2008; 28:379-387.

Kornmann M, Kleeff J, Debinski W, Korc M. Pancreatic cancer cells express interleukin-13 and -4 receptors, and their growth is inhibited by *Pseudomonas* exotoxin coupled to interleukin-13 and -4. Anticancer Res. 1999; 19:125-131.

Leen A M, Christin A, Myers G D et al. Cytotoxic T lymphocyte therapy with donor T cells prevents and treats adenovirus and Epstein-Ban virus infections after haploidentical and matched unrelated stem cell transplant. Blood 2009

Leen A M, Myers G D, Sili U et al. Monoculture-derived T lymphocytes specific for multiple viruses expand and produce clinically relevant effects in immunocompromised individuals. Nat. Med. 2006; 12:1160-1166.

Leen A M, Rooney C M, Foster A E. Improving T cell therapy for cancer. Annu. Rev. Immunol. 2007; 25:243265.

Lepisto A J, Moser A J, Zeh H et al. A phase 1/11 study of a MUC1 peptide pulsed autologous dendritic cell vaccine as adjuvant therapy in patients with resected pancreatic and biliary tumors. *Cancer Ther.* 2008; 6:955-964.

Li M, Bharadwaj U, Zhang R et al. Mesothelin is a malignant factor and therapeutic vaccine target for pancreatic cancer. Mol. Cancer Ther. 2008; 7:286-296.

Louis C U, Straathof K, Bollard C M et al. Enhancing the in vivo expansion of adoptively transferred EBV specific CTL with lymphodepleting CD45 monoclonal antibodies in NPC patients. Blood 2009; 113:24422450.

Morgan R A, Dudley M E, Wunderlich J R et al. Cancer regression in patients after transfer of genetically engineered lymphocytes. Science 2006; 314:126-129.

Nakazawa Y, Huye L E, Dotti G et al. Optimization of the PiggyBac Transposon System for the Sustained Genetic Modification of Human T Lymphocytes. J Immunother 2009

Plate J M. Current immunotherapeutic strategies in pancreatic cancer. Surg. Oncol. Clin. N. Am. 2007; 16:91943, xi.

Prokopchuk 0, Liu Y, Henne-Bruns D, Kornmann M. Interleukin-4 enhances proliferation of human pancreatic cancer cells: evidence for autocrine and paracrine actions. Br. J. Cancer 2005; 92:921-928.

Quintarelli C, Vera J F, Savoldo B et al. Co-expression of cytokine and suicide genes to enhance the activity and safety of tumor-specific cytotoxic T lymphocytes. Blood 2007; 110:2793-2802.

Rong Y, Jin D, Wu W et al. Induction of protective and therapeutic anti-pancreatic cancer immunity using a reconstructed MUC1 DNA vaccine. BMC. Cancer 2009; 9:191.

Rooney C M, Smith C A, Ng C et al. Use of gene-modified virus-specific T lymphocytes to control Epstein-Barr virus-related lymphoproliferation. Lancet 1995; 345:9-13.

Savoldo B, Rooney C M, Di S A et al. Epstein Barr virus specific cytotoxic T lymphocytes expressing the anti-CD30zeta artificial chimeric T-cell receptor for immunotherapy of Hodgkin disease. Blood 2007; 110:2620-2630.

Seicean A, Popa D, Mocan T, Cristea V, Neagoe I. Th1 and Th2 profiles in patients with pancreatic cancer compared with chronic pancreatitis. Pancreas 2009; 38:594-595.

Seruga B, Zhang H, Bernstein L J, Tannock I F. Cytokines and their relationship to the symptoms and outcome of cancer. Nat. Rev. Cancer 2008; 8:887-899.

Straathof K C, Bollard C M, Popat U et al. Treatment of nasopharyngeal carcinoma with Epstein-Barr virus-specific T lymphocytes. Blood 2005; 105:1898-1904.

Sweeney A D, Wu M F, Hilsenbeck S G, Brunicardi F C, Fisher W E. Value of pancreatic resection for cancer metastatic to the pancreas. J. Surg. Res. 2009; 156:189-198.

Tanis P J, van der Gaag N A, Busch O R, van Gulik T M, Gouma D J. Systematic review of pancreatic surgery for metastatic renal cell carcinoma. Br. J. Surg. 2009; 96:579-592.

Tassi E, Gavazzi F, Albarello L et al. Carcinoembryonic antigen-specific but not antiviral CD4+ T cell immunity is impaired in pancreatic carcinoma patients. J. Immunol. 2008; 181:6595-6603.

Vera J, Savoldo B, Vigouroux S et al. T lymphocytes redirected against the kappa light chain of human immunoglobulin efficiently kill mature B lymphocyte-derived malignant cells. Blood 2006; 108:3890-3897.

Vera J F, Brenner L J, Gerdemann U et al. Accelerated production of antigen-specific T-cells for pre-clinical and clinical applications using Gas-permeable Rapid Expansion cultureware (G-Rex). J Immunother 2009; In press:

Vera J F, Hoyos V, Savoldo B et al. Genetic manipulation of tumor-specific cytotoxic T lymphocytes to restore responsiveness to IL-7. Mol. Ther. 2009; 17:880-888.

Voidonikolas G, Gingras M C, Hodges S et al. Developing a tissue resource to characterize the genome of pancreatic cancer. World J. Surg. 2009; 33:723-731.

Wong H H, Lemoine N R. Pancreatic cancer: molecular pathogenesis and new therapeutic targets. Nat. Rev. Gastroenterol. Hepatol. 2009; 6:412-422.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of treating cancer in an individual, comprising the steps of delivering by direct injection into a cancer in the individual a therapeutically effective amount of autologous T cells comprising:
   (1) a chimeric cytokine receptor comprising a cytokine binding exodomain and a signal transducing endodomain, wherein the chimeric cytokine receptor comprises an interleukin-4 (IL-4) receptor exodomain and an IL-7 receptor endodomain, and
   (2) a chimeric antigen receptor that targets an antigen expressed by said cancer;
   wherein the cancer expresses IL-4.

2. The method of claim 1, wherein the cancer is pancreatic cancer, lung cancer, or breast cancer.

3. The method of claim 1, wherein the T cells are cytotoxic T cells.

4. The method of claim 3, wherein the T cells target prostate-specific cancer antigen (PSCA), carcinoembryonic antigen (CEA), mucin 1 (MUC1), mucin 5AC (MUC5AC), mucin 6 (MUC6), telomerase, preferentially expressed antigen in melanoma (PRAME), Melanoma antigen E A (MAGE-A), synovial sarcoma X 2/4 (SS X2/4), New York-esophageal cancer-1 (NY-ESO), or Survivin.

5. The method of claim 1, wherein said chimeric cytokine receptor is expressed from a retroviral vector, lentiviral vector, or transposon plasmid in said cell.

6. A method of claim 1, wherein the T cells are Epstein Barr Virus (EBV) specific.

* * * * *